United States Patent
Morris et al.

(10) Patent No.: US 10,426,890 B2
(45) Date of Patent: Oct. 1, 2019

(54) DRUG DELIVERY DEVICE

(71) Applicant: Sanofi-Aventis Deutschland GmbH, Frankfurt am Main (DE)

(72) Inventors: Anthony Paul Morris, West Midlands (GB); Joseph Butler, Rugby (GB); David Plumptre, Worcestershire (GB); Matthew Meredith Jones, Warwickshire (GB); Robert Frederick Veasey, Warwickshire (GB); Neal Alexander Blundred, West Midlands (GB); Samuel Keir Steel, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 88 days.

(21) Appl. No.: 15/310,188

(22) PCT Filed: May 27, 2015

(86) PCT No.: PCT/EP2015/061631
§ 371 (c)(1),
(2) Date: Nov. 10, 2016

(87) PCT Pub. No.: WO2015/181194
PCT Pub. Date: Dec. 3, 2015

(65) Prior Publication Data
US 2017/0157325 A1    Jun. 8, 2017

(30) Foreign Application Priority Data
May 28, 2014 (EP) .................. 14170330

(51) Int. Cl.
*A61M 5/19* (2006.01)
*A61M 5/24* (2006.01)
*A61M 5/315* (2006.01)

(52) U.S. Cl.
CPC ............ *A61M 5/19* (2013.01); *A61M 5/2448* (2013.01); *A61M 5/3155* (2013.01);
(Continued)

(58) Field of Classification Search
CPC .... A61M 5/19; A61M 5/2448; A61M 5/3155; A61M 5/31551; A61M 5/3158; A61M 5/31593
See application file for complete search history.

(56) References Cited

FOREIGN PATENT DOCUMENTS

| | | |
|---|---|---|
| GB | 2497375 | 6/2013 |
| JP | 2013-523198 | 6/2013 |

(Continued)

OTHER PUBLICATIONS

International Preliminary Report on Patentability in International Application No. PCT/EP2015/061631, dated Nov. 29, 2016, 6 pages.

(Continued)

*Primary Examiner* — Imani N Hayman
(74) *Attorney, Agent, or Firm* — Fish & Richardson P.C.

(57) ABSTRACT

The invention is directed to drug delivery device comprising a primary drug delivery assembly (3) with a primary dose dial sleeve (17) and a secondary drug delivery assembly (4) with a secondary drive sleeve (24). For user selection, a selection switch (48) is movable between a first, a second and a third position and a clutch (49) is connected to the selection switch (48) such that movement of the selection switch (48) causes rotation of the clutch (49). A secondary drive sleeve (24) is configured to rotate and to engage the clutch (49), wherein the clutch (49) is configured to transfer rotation to the secondary drive sleeve (24) when the selection switch (48) is moved from the first position into the
(Continued)

Figure 1:
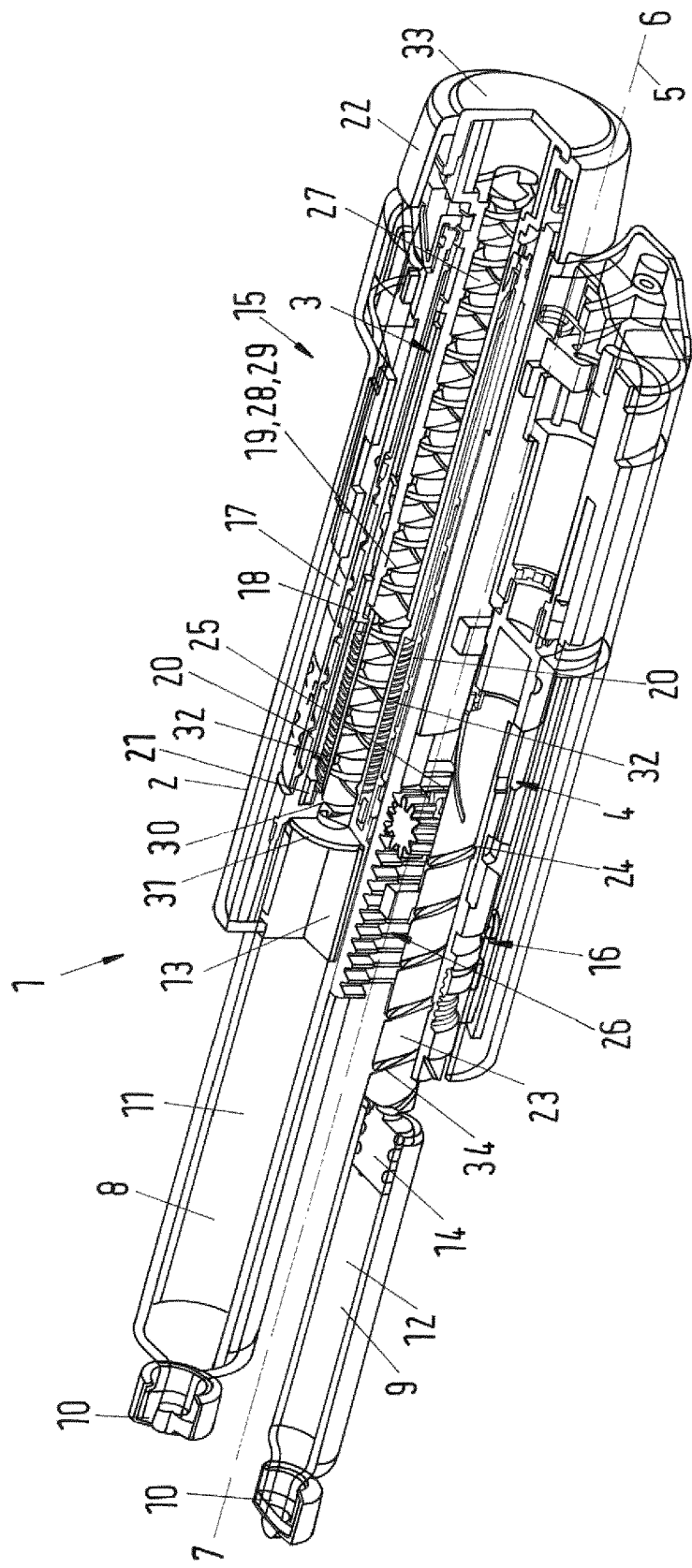

second position and to disengage from the secondary drive sleeve (24) when the selection switch (48) is moved from the first into the third position.

12 Claims, 16 Drawing Sheets

(52) U.S. Cl.
CPC ...... *A61M 5/3158* (2013.01); *A61M 5/31551* (2013.01); *A61M 5/31593* (2013.01)

(56) References Cited

FOREIGN PATENT DOCUMENTS

| | | |
|---|---|---|
| JP | 2013-544159 | 12/2013 |
| JP | 2013-544160 | 12/2013 |
| JP | 2013-544169 | 12/2013 |
| WO | WO 2011/117287 | 9/2011 |
| WO | WO 2012/072553 | 6/2012 |
| WO | WO 2012/072554 | 6/2012 |
| WO | WO 2012/072569 | 6/2012 |

OTHER PUBLICATIONS

International Search Report and Written Opinion in International Application No. PCT/EP2015/061631, dated Aug. 24, 2015, 8 pages.

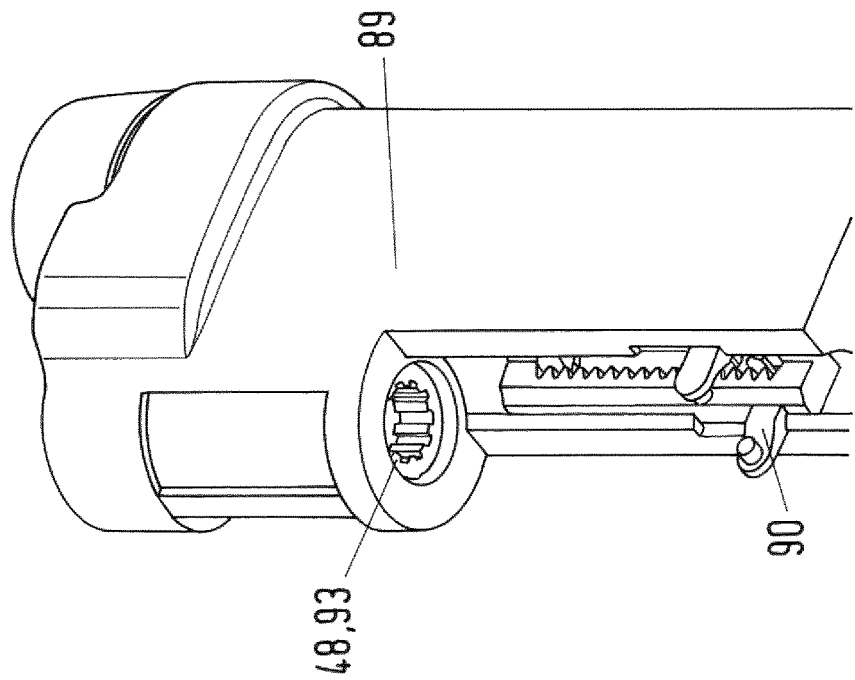
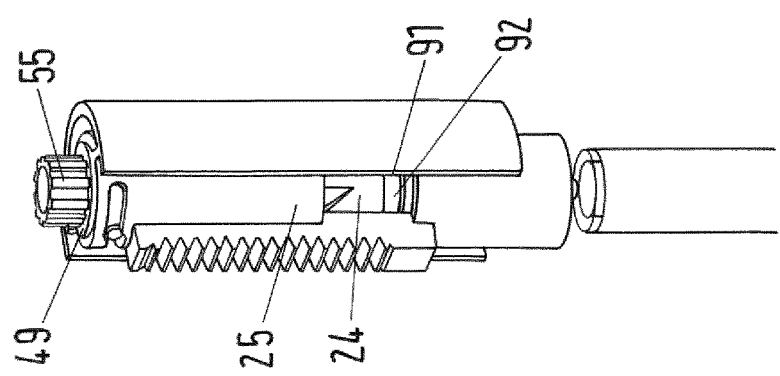
Fig.16b
Fig.16a

DRUG DELIVERY DEVICE

CROSS-REFERENCE TO RELATED APPLICATIONS

This application is a National Stage application under 35 U.S.C. § 371 of International Application No. PCT/EP2015/061631, filed May 27, 2015, which claims the benefit of EP Application No. 14170330.6, filed on May 28, 2014. The disclosures of the prior applications are incorporated by reference in their entirety.

The present invention is directed to a drug delivery device with a primary drug delivery assembly and a secondary drug delivery assembly.

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Another example of a medicament combination is the administration of a pain reliever in combination with a medicament for treating osteoarthritis.

Drug delivery devices of the aforementioned kind often have applications where regular injection by persons without formal medical training occurs. This is increasingly common among patients having diabetes or the like, e.g. osteoarthritis. Self-treatment enables such patients to conduct effective management of their disease.

In combination therapy, a primary medicament and a secondary medicament are delivered in a specific relationship to deliver the optimum therapeutic dose. The injection devices of the generic kind usually comprise a housing in which two or more drug delivery assemblies are retained. Such devices include a primary drug delivery assembly for dispensing the primary medicament such as the long-acting insulin and a secondary drug delivery assembly for dispensing the secondary medicament, such as GLP-1. Some kinds of drug delivery assemblies comprise a compartment such as a cartridge holder for accommodating a replaceable medicament container such as a cartridge which stores the medicament.

In some cases, depending on the patient or the stage of the therapy, an effective treatment requires variations in the quantities and/or proportions of the medicaments making up the combined therapy. For example, the patient may require a non-adjustable fixed dose of the secondary medicament in combination with an adjustable variable dose of the primary medicament.

The effectiveness of a combined delivery of medicaments may require one or more doses to be delivered sequentially with one of the two medicaments being injected into the human body prior to the delivery of the other medicament. Such treatment may be conducted with devices that include two separate dispensing mechanisms that are actuated independently from each other such that the dispensing mechanisms are activated successively. Sometimes patients require merely a dose of one of the medicaments, e.g. the primary medicament. The correct use of the device, however, may be hazardous for patients that are physically or mentally impaired or otherwise disadvantaged. It is desirable to have a device that is simple in terms of use and that has a high degree of user safety.

It is an object of the invention to improve the setting capabilities of a drug delivery device of the aforementioned kind and to provide a high degree of user convenience and safety. In particular, it is desired to enable the user to choose either to dispense a dose of only one the medicaments or a combined dose of both medicaments.

The above problem is solved by a drug delivery device as defined in claim 1.

Drug delivery devices of the aforementioned kind comprise a primary drug delivery assembly with a primary dose dial sleeve and a secondary drug delivery assembly with a secondary drive sleeve. According to the invention, a selection element, such as a selection switch is provided that is movable between a first position, a second position and a third position. A clutch is connected to the selection switch such that movement of the selection switch causes rotation of the clutch. A secondary drive sleeve is configured to rotate and to engage the clutch preferably during dose setting of the secondary drug delivery assembly. According to the invention, the clutch is configured to transfer rotation of the clutch to the secondary drive sleeve when the selection switch is moved from the first position into the second position and to disengage from the secondary drive sleeve when the selection switch is moved from the first into the third position such that rotation of the clutch and movement of the selection switch is not transferred to the secondary drive sleeve.

Preferably the selection switch is rotateable, preferably around a longitudinal axis that runs in axial direction of the secondary drive sleeve between the first, the second and the third position and the clutch is rotationally constrained to the selection switch.

The mechanism provides an efficient control interface to the user. With the selection switch interface the user can easily choose only to set and inject a dose of a primary medicament in the primary drug delivery assembly or to set a combined dose of the primary medicament and a secondary medicament in the secondary drug delivery assembly. The user has optimal conditions for combined therapy treatment. The selection switch may be formed as a lever or may be connected to a lever element for convenient operation such that the user can operate the selection switch from the outside of the drug delivery device housing.

The drug delivery housing may extend from a proximal end to a distal end along a longitudinal axis and accommodate the primary and the secondary drug delivery assembly. The distal end is usually referred to as the dispensing end where the drug delivery device may be equipped with a single dispense interface, such as a needle hub with an injection needle. The proximal end is usually referred to as the actuation end where a user presses a button or the like to start injection.

Preferably, the clutch is in splined engagement with the selection switch. The splined connection between the selection switch and the clutch may be formed such that rotational movement of the selection switch is transferred to the clutch while the clutch is axially moveable relative to the selection switch, preferably along a longitudinal axis that extends from the proximal end of the drug delivery device to the distal end. The clutch may comprise a number of axially extending ribs or the like that engage a number of axially extending grooves on the selection switch.

Preferably, the secondary drive sleeve is configured to move proximally in a helical movement during dose setting and to move distally in a pure axial motion during dose dispense. A helical movement can be characterized as a movement of combination of a longitudinal motion in combination with a rotation about the axis of motion.

Preferably, the primary number sleeve is configured to move proximally a helical movement during dose setting and to move distally in the opposite direction in an opposite helical movement during dose dispense.

The primary drug delivery assembly may be retained in or attached to the drug delivery device housing and may be configured such as to deliver a variable dose of a primary medicament and the secondary drug delivery assembly may be retained in or attached to the drug delivery device housing and may be configured to deliver only a fixed dose of a secondary medicament. The primary and the secondary drug delivery assembly may each contain a medicament reservoir and may be configured for dose setting and dose dispense of the respective medicament. A primary medicament, e.g. a long-acting insulin may be contained in the primary reservoir and a secondary medicament, e.g. GLP-1, may be contained in the secondary reservoir.

The primary drug delivery assembly may comprise a primary dose setting mechanism and a primary dose dispense mechanism. The secondary drug delivery assembly may comprise a secondary dose setting mechanism and a secondary dose dispense mechanism. The drug delivery device may include a variable dose setting mechanism which is associated with the primary drug delivery assembly to set a variable dose of the primary medicament and a fixed dose setting mechanism which is associated with the secondary drug delivery assembly to set a fixed dose of the secondary medicament. The primary drug delivery assembly and the secondary drug delivery assembly may each extend along a longitudinal axis running parallel to the longitudinal axis of the housing The primary drug delivery assembly may include a primary drug delivery assembly housing. Alternatively, the housing of the drug delivery device may constitute the primary drug delivery assembly housing. The secondary drug delivery assembly may include a secondary drug delivery assembly housing. Alternatively, the housing of the drug delivery device may constitute the secondary drug delivery assembly housing.

The primary drug delivery assembly may further comprise an actuation element such as a dose setter or a dose dial grip configured to be rotationally fixed to the primary dose dial sleeve during dose setting such that rotation of the actuation element causes the primary dose dial sleeve to rotate and to wind out of the housing in a combination of translational and rotational movement.

Preferably, the primary dose dial sleeve comprises a number of indices for visually indicating the set dose. Accordingly, the primary dose dial sleeve may be referred to as the primary number sleeve.

The term "fixed dose" as used herein can be characterized as a dose value that is defined by the construction of the drug delivery assembly, wherein the user is only able to inject a specific dose. The user is not in the position to set lower or higher doses of medicament and/or to inject lower or higher doses of the medicament. The dose the user may effectively set and inject is restricted to a certain value.

On the contrary, the term "variable dose" can be characterized as a dose where the user is substantially free to choose the amount of medicament he wants to inject. The dose is variably adjustable, normally between upper and lower limits.

The selection switch may be rotatable between three positions. The first position may be an intermediate "at rest" or central position between the second and the third position in rotational direction. The selection switch may be rotated along an axis extending from the proximal to the distal end of the device. The selection switch may be rotated in clockwise and counterclockwise direction of the device when looking from the proximal end of the device to the distal end of the device.

From the "at rest" position, the selection switch may be rotated into the second position, which may be referred to as the "fixed dose on" position as the movement of the selection switch is transferred to the secondary drive sleeve. Rotation of the secondary drive sleeve comes along with the setting of a dose of the secondary medicament. In the "fixed dose on" position a combined dose of the primary medicament and the secondary medicament may be set and administered.

From the "at rest" position, the selection switch may be moved into the third position, which may be referred to as the "fixed dose off" position as the clutch is decoupled from the secondary drive sleeve and movement of the selection switch is not transferred to the secondary drive sleeve. Without rotation of the secondary drive sleeve no dose of the secondary medicament is set. In the "fixed dose off" position only a dose of the primary medicament can be set.

According to a further embodiment, the clutch is movable between a distal position and proximal axial position, wherein the clutch is rotationally constrained or rotationally fixed to the secondary drive sleeve in the distal position and wherein the clutch is free to rotate relative to the secondary drive sleeve in the proximal position. Preferably, the clutch is in the distal position when the selection switch is in the "at rest" position and/or the "fixed dose on" position and in the proximal position, when the selection switch is in the "fixed dose off" position. The clutch may be positioned substantially proximally from the secondary drive sleeve. The selection switch may be positioned proximally from the clutch.

The clutch may be connected to the secondary drive sleeve via a splined interface which is configured such that relative rotational movement between the clutch and the secondary drive sleeve is prevented while relative axial movement is allowed when the clutch and the secondary drive sleeve are engaged. The clutch may comprise engagement arms provided in a circular formation around a longitudinal axis of the clutch and extending in axial direction towards the secondary drive sleeve. The clutch may have an open distal end and the proximal end of the drive sleeve may be insertable into the opening of the clutch. The proximal end section of the secondary drive sleeve may be provided with a number of axially extending grooves that are open at the proximal end such that the radially inner surface of the engagement arms may enter the grooves. The radially inner surface of the engagement arms and the grooves may form a groove/nut or splined connection so that rotational movement may be transferred between the clutch and the secondary drive sleeve, while allowing relative axial movement.

According to a further embodiment, the clutch is rotationally and axially guided by engagement with a stationary guidance provided by the drug delivery housing or a housing element of the secondary drug delivery assembly. The clutch may be provided with a projection, a pin or any other suitable engagements means that engage into the guidance or an engagement section, such as a groove that is provided stationary in the drug delivery housing. The engagement section may be configured to move the clutch into the proximal position when the selection switch is moved from the first into the third position or "fixed dose off" position while the clutch remains stationary in the axial direction when the selection switch is moved from the first position into the "fixed dose on" position. Thereby, the axial position of the clutch may be constrained by its interface with the housing.

The guidance groove may comprise a first and a second section wherein travel of the pin between the first and the second section may cause the clutch to travel between the distal and the proximal position. The first and the second section may extend in a parallel relationship and transverse to the longitudinal axis of the housing at least partly around the clutch in circumferential direction, e.g. on an inner surface of the drug delivery device housing or on an inner surface of a housing element of the secondary drug delivery assembly.

The first and second section may be separated from each other by a transition such as an inclined surface wherein the pin may run from the first section into the second section via the transition and back. Travel of the pin between the first and the second causes the clutch to move in axial direction. Hereby, a very precise control of the dose setting mechanism of the secondary drug delivery assembly is provided.

According to a further embodiment of the invention, the splined connection between the clutch and the secondary drive sleeve comprises a ratchet. This ensures that the travel of the pin in the transition area does not cause rotation of the secondary drive sleeve during disengagement of the clutch and the secondary drive sleeve. For example, at the proximal end of the grooves of the secondary drive sleeve, inclined surface areas formed as ratchet elements may be provided to enable the clutch to rotate relative to the secondary drive sleeve when the clutch moves from the distal into the proximal position.

According to a further embodiment of the invention, the selection switch is configured to transfer movement to the primary dose dial sleeve such that actuation of the selection switch causes the primary dose dial sleeve to rotate. Preferably, movement of the selection switch from the first position into the second position and movement from the first position into the third position causes the primary dose dial sleeve to rotate in the same direction, e.g. clockwise direction. The mechanism efficiently connects the choice of the user between a single dose or a combined dose with an automatic setting of a dose of the primary medicament. From the "at rest" position, the user operates the selection switch to set the device to deliver a fixed dose of the secondary medicament in combination with a variable dose of the primary medicament or to deliver a variable dose of the primary medicament only.

When the selection switch is moved from the first into the second position ("fixed dose on"), movement of the selection switch is transferred to the secondary drive sleeve and the primary dose dial sleeve. By actuating the selection switch, a predetermined dose of the primary medicament and a predetermined dose of the secondary medicament are set. On the contrary, when the selection switch is moved from the first into the third position ("fixed dose off"), movement of the selection switch is only transferred to the primary dose dial sleeve and a dose of the secondary medicament is not set. In each case, the selection movement of the selection switch from the first position into the second position or into the third position causes the setting of a dose of medicament in the primary drug delivery assembly.

Further, the mechanism enables the user to turn off the fixed dose in the secondary drug delivery assembly and to 'split' their dose. i.e. take part of their dose from the end of the cartridge of one device and the other part from a new device, without receiving two doses of fixed dose medicament. The automatic dialing of a predetermined units of a primary medicament in the primary drug delivery assembly ensures that the needle hub is always flushed with variable dose medicament at the end of delivery.

The selection switch may be provided with means to define the possible degree of movement, resp. rotation. On the outer surface of the selection switch, a selection bar may be provided. The selection bar may extend in axial direction of the selection switch and may be configured to engage a stationary counter abutment, e.g. a projection formed on the inner surface of the housing. The maximum value of rotational movement of the selection switch from the "at rest" position in clockwise direction ("fixed dose on") as well as in counterclockwise direction ("fixed dose off") can be limited by the selection bar engaging abutment surfaces on the housing.

According to a further embodiment, the drug delivery device comprises a first engagement element that is configured to rotate the primary dose dial sleeve in one direction and that is adapted to engage or to be engaged by the selection switch such that movement of the selection switch from the first position into the second position and from the first position into the third position causes the first engagement element to rotate the primary dose dial sleeve in the one direction, respectively the same direction.

Preferably the one direction is the dose dial direction into which the primary dose dial sleeve is usually rotated to set a dose of the primary medicament. The opposite direction is usually the direction in which the primary dose dial sleeve rotates during unsetting or during dispense of the primary medicament.

An efficient automatic setting mechanism is provided by which the primary dose dial sleeve may be advanced a predetermined number of units during setting of the dose of the secondary medicament and before the user directly operates the dose dial grip of the primary dose dial sleeve. Regardless the direction into which the selection switch is rotated from the "at rest" position, the primary dose dial sleeve is always rotated in the same direction and a predetermined dose of the primary medicament is set. The automatically set size of the dose of the primary medicament may be determined by the length of the movement of the selection switch, so that said automatically set dose can easily be pre-set by constructive measures that define the degree of rotation of the primary dose dial sleeve.

A further embodiment of the invention concerns a drug delivery device comprising a primary drug delivery assembly with a primary dose dial sleeve configured to move proximally in a helical movement during setting of a dose of a primary medicament contained in a primary reservoir of the primary drug delivery assembly and a secondary drug delivery assembly with a secondary drive sleeve configured to move in a proximal direction in a helical movement during setting of a dose of a secondary medicament contained in a secondary reservoir of the secondary drug delivery assembly. The drug delivery device comprises a selection switch rotateable between a first, a second and a third position, wherein the first position is an intermediate position between the second and the third position; a clutch rotationally constrained to the selection switch such that movement of the selection switch causes rotation of the clutch, wherein the secondary drive sleeve is configured to rotate and to engage the clutch, wherein the clutch is configured to transfer rotation to the secondary drive sleeve when the selection switch is moved from the first position into the second position such that a dose of the secondary medicament is set and to disengage from the secondary drive sleeve when the selection switch is moved from the first into the third position such that a dose of the secondary medicament is not set. The drug delivery device further comprises a first engagement element that is configured to rotate the primary dose dial sleeve, e.g. by engagement, in one direction before the primary dose dial sleeve has been rotated to set a dose, wherein the first engagement element is adapted to be engaged by the selection switch such that movement of the selection switch from the first position into the second position as well as movement of the selection switch from the first position into the third position causes the first engagement element to rotate the primary dose dial sleeve in the one direction such that a predetermined dose of the primary medicament is set. The above means that regardless of the switching direction of the selection switch, from the first position into the second position or from first position into the third position, it causes the setting of an increasing, in particular pre-set dose of the primary medicament.

The user of the drug delivery device may choose to set a dose of the secondary medicament in combination with a dose of the primary medicament or he may choose to set a dose of the primary medicament only by means of the selection switch. In both cases, a predetermined increasing dose of the primary medicament is set by rotation of the primary dose dial sleeve. In order to make sure that the user actuates the selection switch, a limiting mechanism may be included that limits the settable dose of the primary medicament before the user has actuated the selection switch, resp. when the selection switch is still in the first position. According to this embodiment, the first engagement element comprises a third engagement section for engagement with a boss on the primary dose dial sleeve when the selection switch is in the first position such that rotation of the primary dose dial sleeve in the one direction to set an increasing dose of the primary medicament is limited.

To enable further dose setting, the user has to actuate the selection switch and to choose if he intends to set a dose of the secondary medicament or not. For this purpose, according to a further embodiment of the invention, the third engagement section, which may be referred to as a locking element, may be arranged on the first engagement element such that when the first engagement element moves from the first into the second position or when the selection switch moves from the first into the second or the third position, further rotation of the dose dial sleeve above the limited value is allowed. It is pointed out that the user can, of course, operate the selection switch prior to the setting of a dose of the primary medicament, e.g. by rotation of a dose dial grip that is connected with the primary dose dial sleeve. In this case, the rotation of the dose dial sleeve is not limited by the third engagement section and the user may set the desired dose of the primary medicament directly. On the other hand, if the primary dose dial sleeve has been rotated prior to actuation of the selection switch and the primary dose dial sleeve cannot be rotated further because the primary dose dial sleeve is locked against further rotation in dose dial direction, rotation of the selection switch from the first into the second or the third position such that the third engagement section disengages from the primary dose dial sleeve, respectively from the boss, allows further rotation of the primary dose dial sleeve to set a higher dose of the primary medicament.

The first engagement element may be formed as a lever and may be rotationally supported in the drug delivery housing so that the first lever can swivel or articulate around an axis that runs parallel to the longitudinal axis of the housing. Accordingly, the first engagement element may be referred to as the first advance lever.

According to a further embodiment, the first engagement element is movable between a first and a second position. The first engagement element may be movable and/or rotatable resp. switchable between the first and the second position. The first engagement element may be configured to rotate the number sleeve in the one direction when moved from the first into the second position.

According to a further embodiment, the first engagement element comprises a first engagement section configured to engage a first counter engagement surface on the primary dose dial sleeve such that movement of the first engagement element from the first into the second position is transferred to the primary dose dial sleeve which is then caused to rotate in the one, preferably dose dialing direction.

The first engagement section may be a projection formed on a first leg of the first engagement element and configured to engage a first counter engagement section such as a projection or an abutment surface provided on the primary number sleeve, wherein when moved from the first into the second position, the first engagement element engages the primary number sleeve and causes the number sleeve to rotate.

The first engagement element may be configured to articulate about an axis such as an axis that runs parallel to the longitudinal axis of the number sleeve between the first position and the second position, wherein in the second position, the first engagement section may engage the first counter engagement surface of the number sleeve such that movement of the first engagement element from the first into the second position is transferred to the number sleeve.

Preferably, the selection switch moves the first engagement element from the first into second position when the selection switch moves from the first position into the second position and from first position into the third position such that the primary dose dial sleeve is rotated in the one direction.

According to a further embodiment, the drug delivery device comprises a second engagement element. The second engagement element may be arranged between the selection switch and the first engagement element and may be configured to transfer movement of the selection switch to the first engagement element. Preferably the second engagement element is configured such that it only transfers movement to the first engagement element when the selection switch is moved from the first into the second position, resp. into the "fixed dose on" position. Accordingly, the second engagement element may be configured to transfer the movement of the selection switch from the first into the second position to the first engagement element such that the primary dose dial sleeve is rotated in the one direction.

The second engagement element may be a coupling or transfer element. When selection switch is moved from the first position into the second position, the selection switch engages the second engagement element, which in turn moves the first engagement element from the first into the second position.

The second engagement element may be formed as a lever and may be rotationally supported in the drug delivery housing so that the second lever can swivel or articulate around an axis that runs parallel to the longitudinal axis of the housing. Accordingly, the second engagement element may be referred to as the second advance lever.

The selection switch may comprise an abutment surface, a projection or the like which engages the second advance lever when the selection switch is moved from the "at rest" position into the "fixed dose on" position, for example in clockwise direction, which causes the second lever to articulate and to engage the first advance lever such that the first advance lever moves from the first into the second position. As a result, the first advance lever engages and advances the number sleeve a number of units such that a dose of the primary medicament is set.

According to a further embodiment, the selection switch preferably directly drives the first engagement element from the first into the second position when the selection switch moves from the first into the third position such that the primary dose dial sleeve is rotated in the one direction. The selection switch may directly engage the first engagement element when the selection switch moves from the first into the third position such that the first engagement element moves from the first into the second position. The selection switch may comprise an abutment surface, a projection or the like which engages the first advance lever when the selection switch is moved from the "at rest" position into the "fixed dose off" position, e.g. by rotation in counterclockwise direction, which causes the first lever to articulate and to move from the first into the second position such that the lever engages and rotates the number sleeve such that a dose of the primary medicament is set. This ensures, that a predetermined dose of the secondary dose is set when the selection switch is moved from the "at rest" position into the "fixed dose off" position.

According to a further embodiment, the first engagement element comprises a second engagement section that engages a stationary counter engagement section in the second position of the first engagement element or the second and/or the third position of the selection switch, wherein the counter engagement section is configured such that the first engagement section disengages from the number sleeve. The counter engagement surface may be arranged such that the first engagement section disengages from the primary dose dial sleeve when the second engagement section engages the stationary counter engagement surface. The second engagement section may be arranged relative to the first engagement section such that engagement between the second engagement section and the counter engagement section causes the first and the second engagement section to move away from the primary dose dial sleeve. The counter engagement surface may be provided on the inner surface of the housing and may be formed as a projection or the like.

The legs of the first engagement element may be flexible so that the engagement sections can be elastically bent away from the primary dose dial sleeve.

According to a further embodiment, the first engagement element comprises a third engagement section and the primary dose dial sleeve comprises an abutment surface such as a boss for engagement with the third engagement section when the selection switch and/or the first engagement element is in the respective first position such that rotation of the primary dose dial sleeve in the one direction is limited. This mechanism limits the primary dose setting mechanism to a predetermined number of units, e.g. 2 units, when the selection switch is in the "at rest" position. Rotation of the primary dose dial sleeve may cause the boss to engage respectively abut the third engagement section after a predetermined degree of relative rotation between the primary dose dial sleeve and the first engagement element or the drug delivery device housing such further rotation of the primary dose dial sleeve in dial direction is prevented. Further, the third engagement section may be arranged on the first engagement element such that the third engagement section disengages from the primary dose dial sleeve, respectively the boss when the first engagement element moves from the first into the second position or when the selection switch moves from the first into the second or the third position ("fixed dose on" or "fixed dose off") such that further rotation of the primary dose dial sleeve is allowed. This efficiently prevents the user from dialing a further dose of the primary medicament with the dose dial grip before the user has actuated the selection switch and set into the second or third position.

The third engagement section may be formed on a second leg of the first engagement element. The first and the second leg may be separated by the rotational support of the first engagement element.

According to a further embodiment, a biasing member such as a spring is provided that is configured to bias the selection switch into the first position. The biasing member may be located on a pivot within the drug delivery device housing and may provide a restoring force to return the selection switch to its centralized "at rest" position.

According to a further embodiment, a latching element is provided that is configured to lock the selection switch in the second and/or the third position. The latching element may be formed as a latch lever and may be rotationally supported in the drug delivery housing so that the latch lever can swivel or articulate around an axis that runs parallel to the longitudinal axis of the housing. The selection switch may comprise detents or the like to engage with a latch on the latch lever.

According to a further embodiment, the primary dose dial sleeve is provided with a means configured to disengage the latching element from the selection switch when the primary dose dial sleeve rotates in a direction opposite the one direction.

The number sleeve may be provided with a ramp feature or the like, which urges the latch lever away from the selection switch when the primary dose dial sleeve rotates in a direction opposite the dose dial direction. The latch lever may engage the selection switch with a first section and may engage the ramp feature with a second section wherein the sections are separated from each other by the rotational support of the latch lever. Accordingly, the ramp feature may cause the latch lever to articulate around the support and may the cause the first section to disengage from the selection switch by urging the second section away from the primary dose dial sleeve.

According to a further embodiment, wherein the primary drug delivery assembly accommodates a primary medicament and the secondary drug delivery assembly accommodates a secondary medicament.

It is preferred, when at least one of the cartridges of the drug delivery device is filled with the medicament. Also, the drug delivery device can be a disposable injection device. Such devices can be thrown away or recycled after the content of the medicament has been exhausted. However, the present invention is also applicable with re-usable devices designed to replace an emptied cartridge with a filled one after the whole content of the former cartridge has been administered.

The term "medicament", as used herein, means a pharmaceutical formulation containing at least one pharmaceutically active compound,
wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 2:
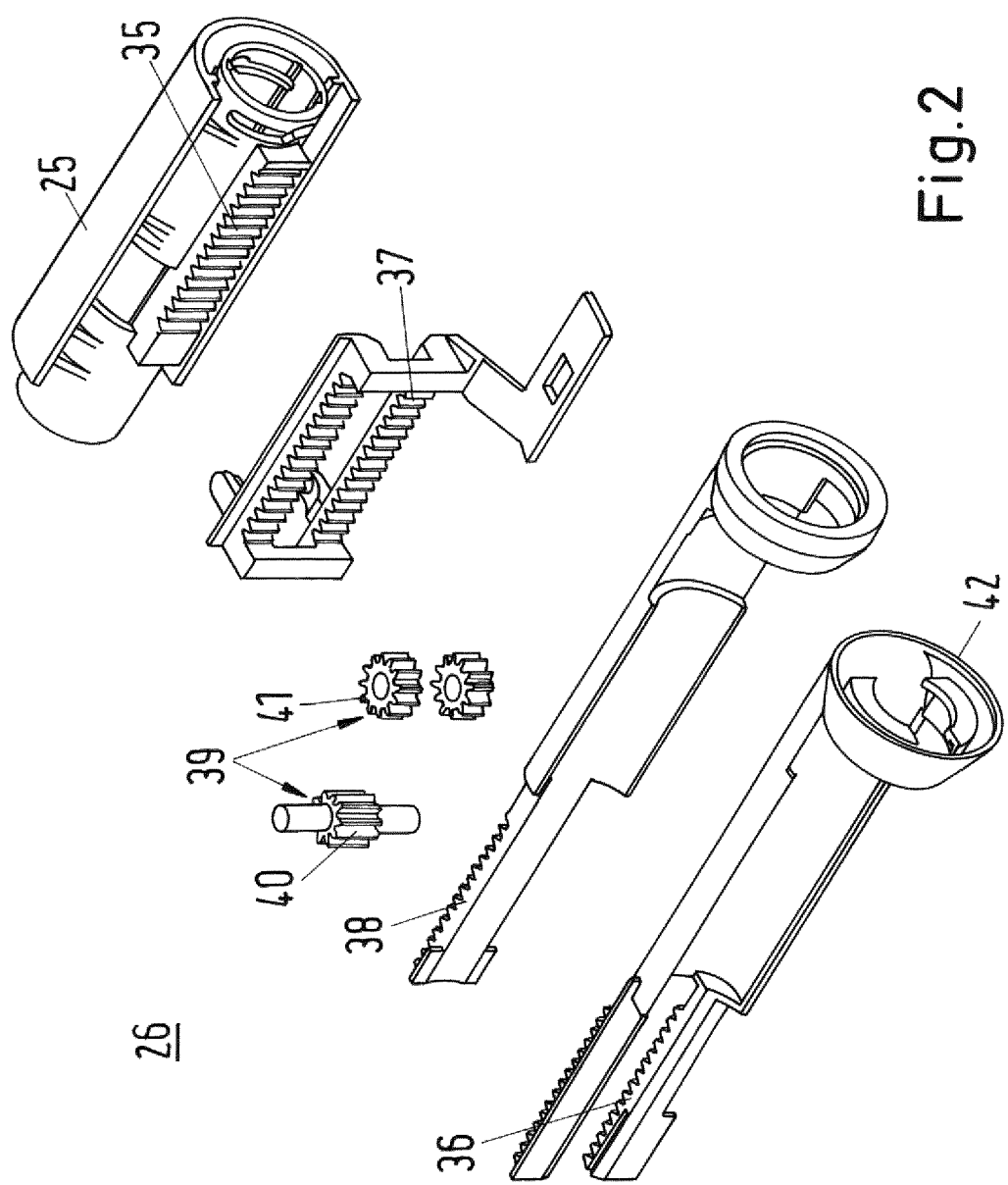
Figure 3:
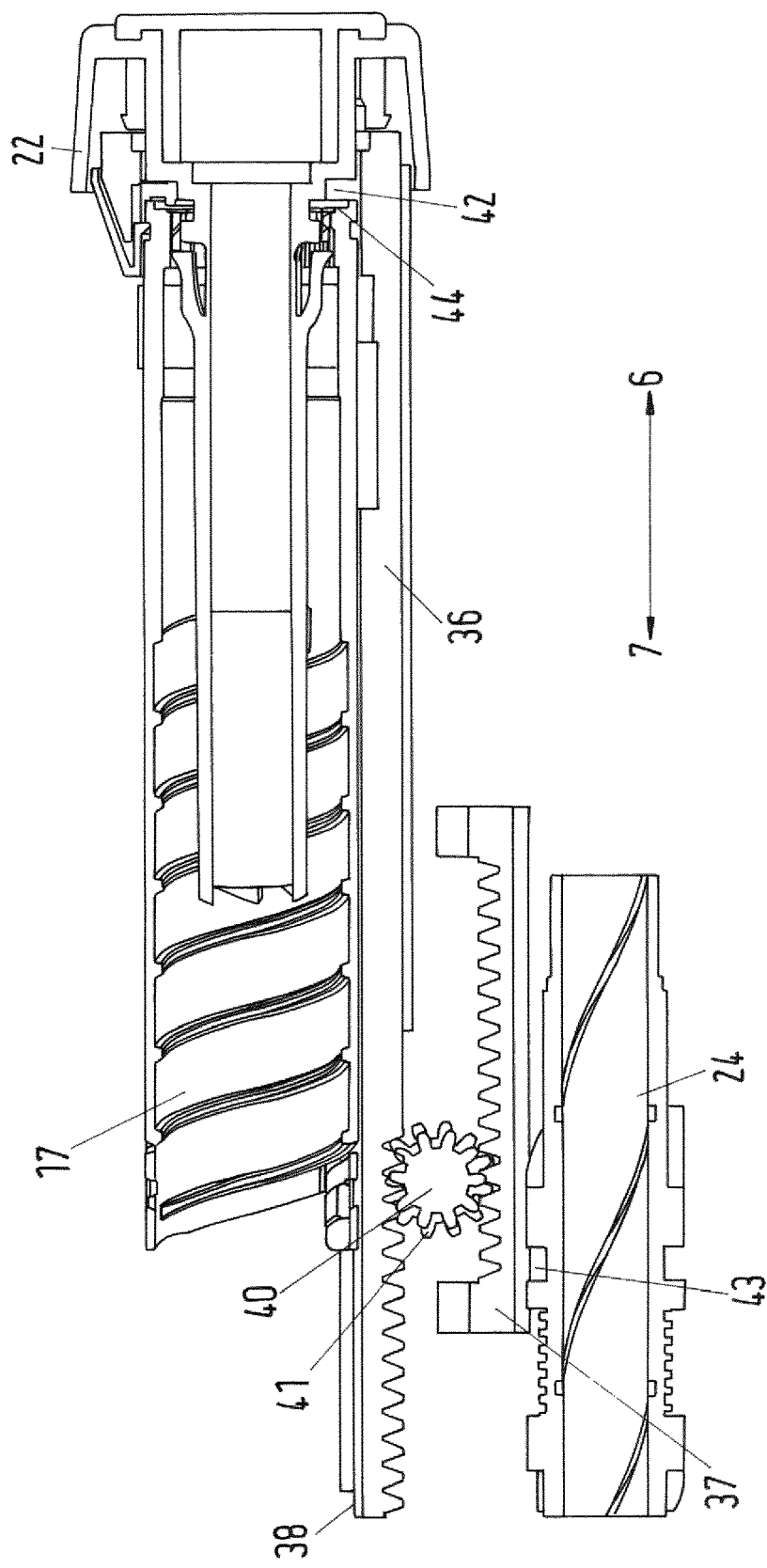
Figure 4:
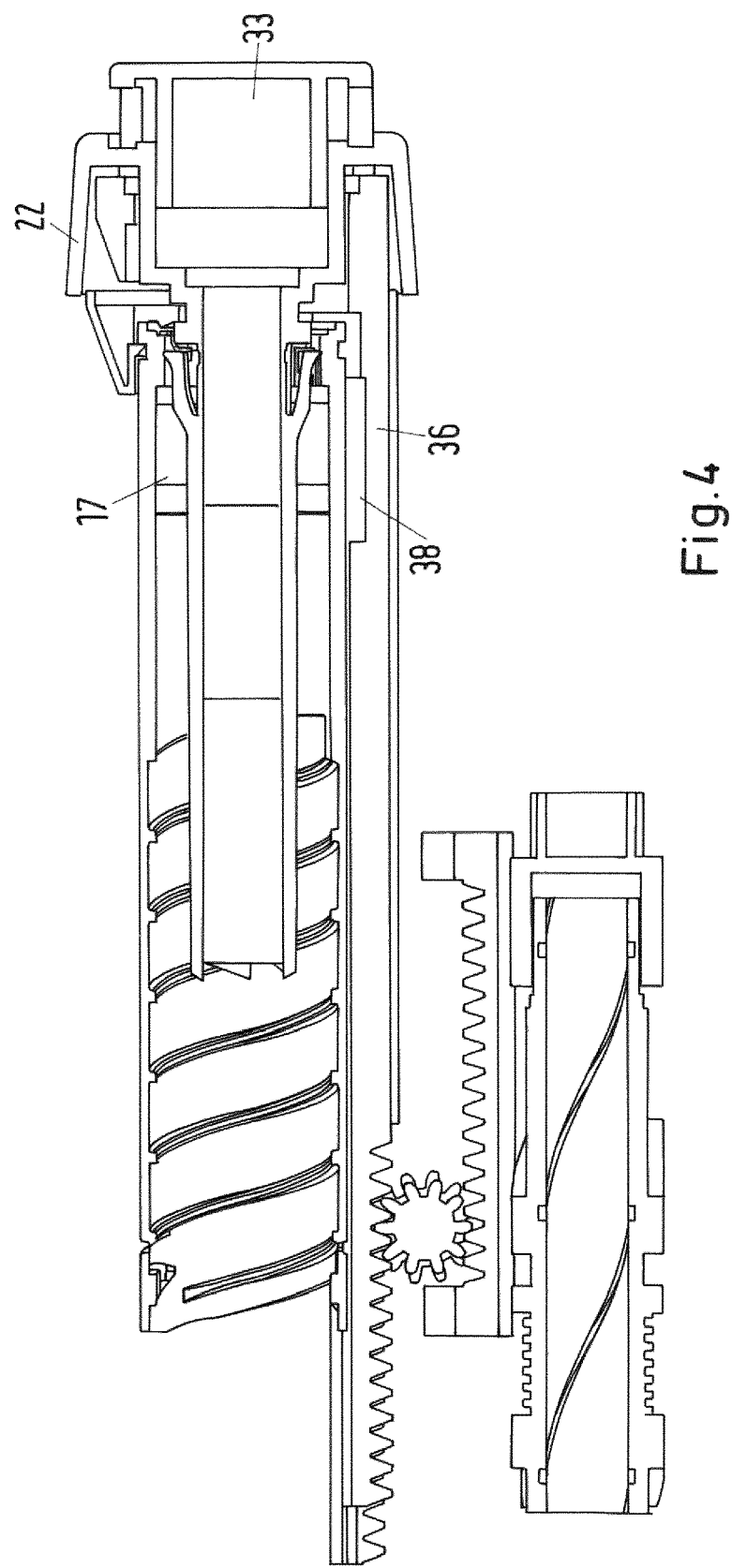
Figure 5:
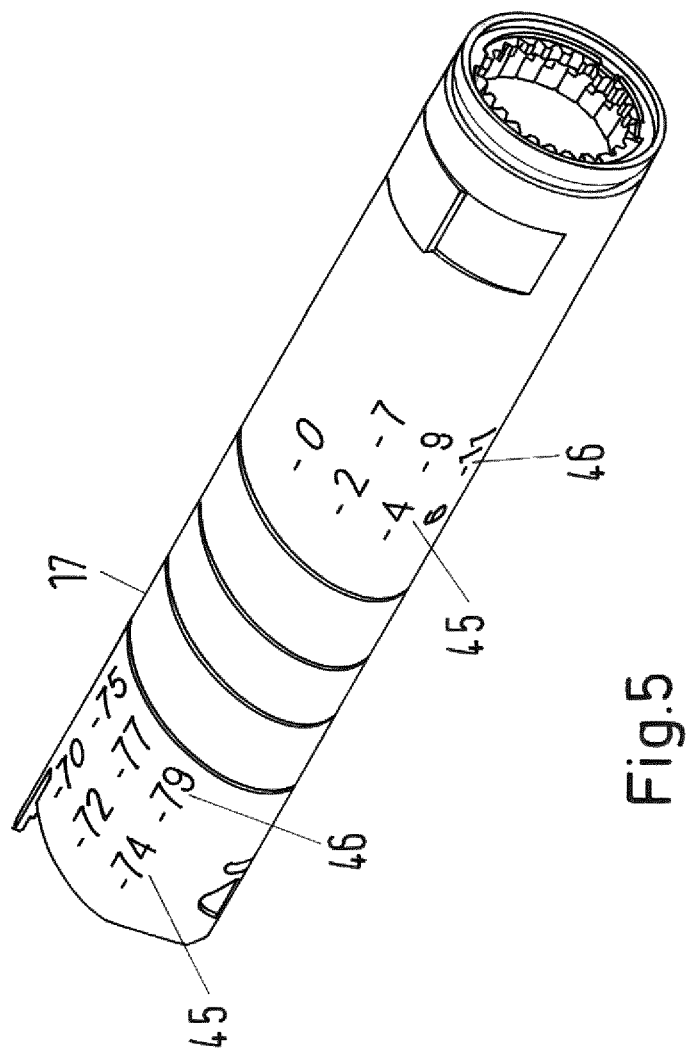
Figure 6:
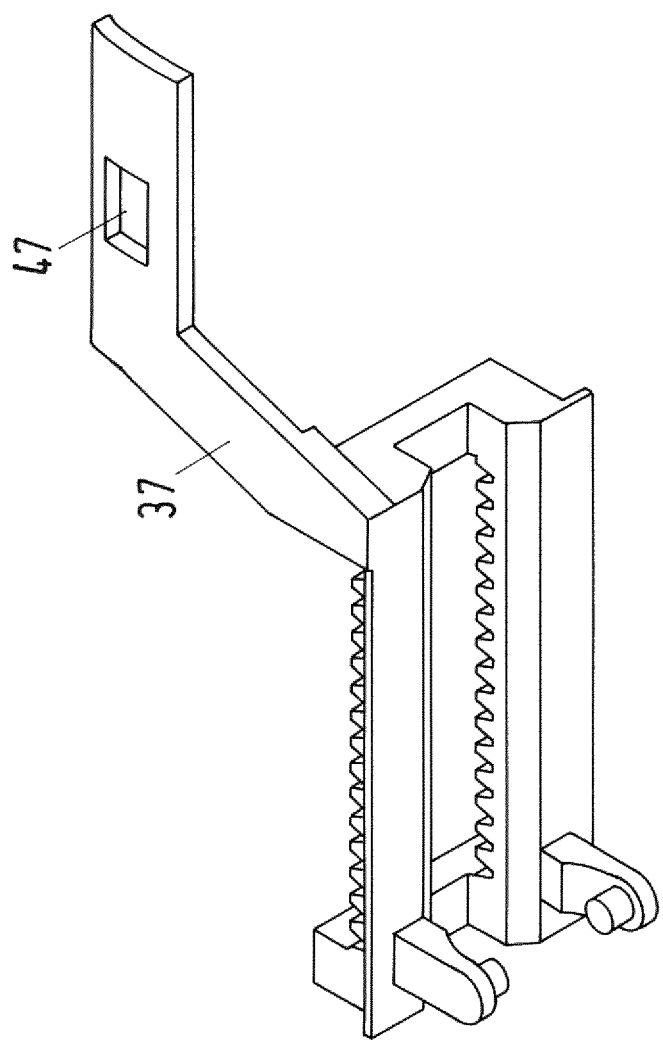
Figure 7:
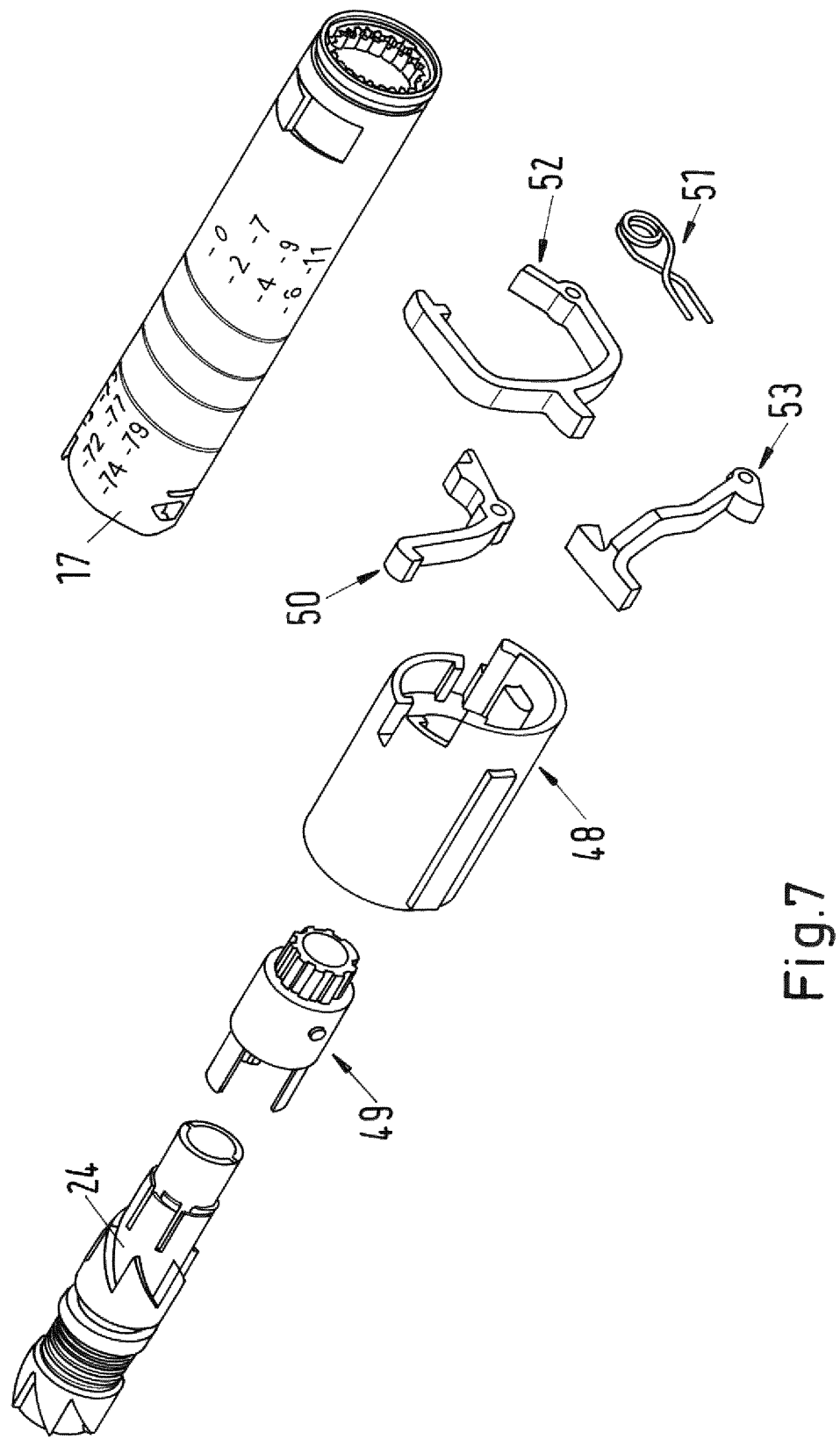

Exemplary embodiments of the invention will now be described with reference to the accompanying drawings, in which:

FIG. 1: shows in perspective sectional view, a drug delivery device in accordance with the present invention;

FIG. 2: shows a perspective view of the components of the differential gear mechanism;

FIG. 3: shows a sectional view of a part of the drug delivery device;

FIG. 4: shows another sectional view of a part of the drug delivery device;

FIG. 5: shows a perspective view of the number sleeve;

FIG. 6: shows a perspective view of the third gear rack;

FIG. 7: shows a perspective view the selection switch assembly

Figure 8:
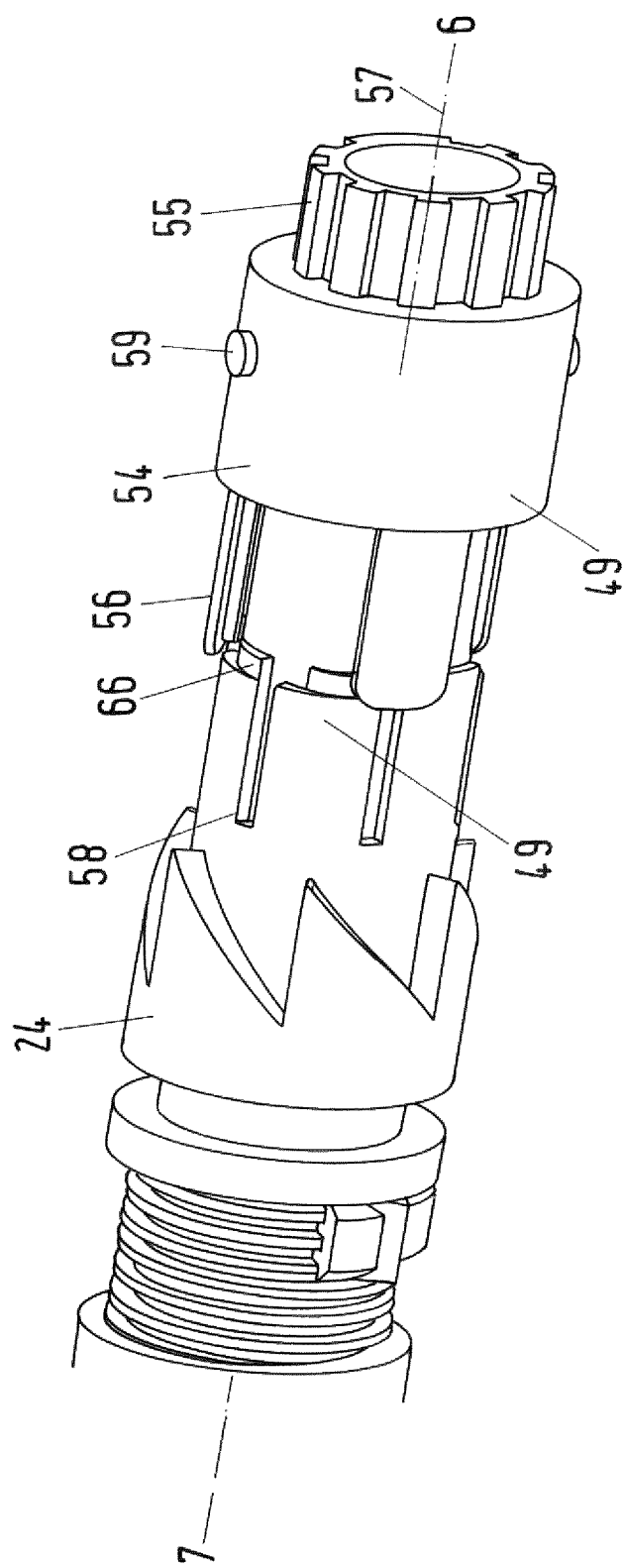
Figure 9:
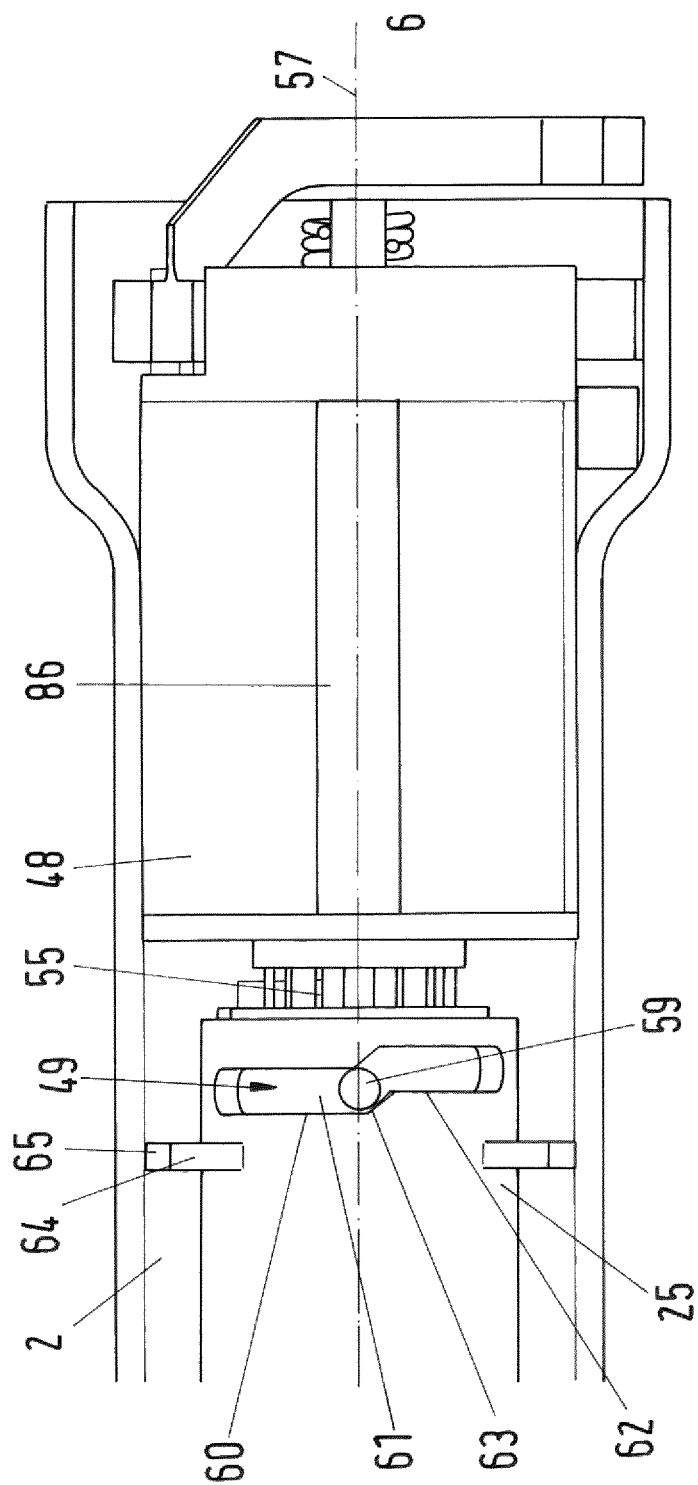
Figure 10:
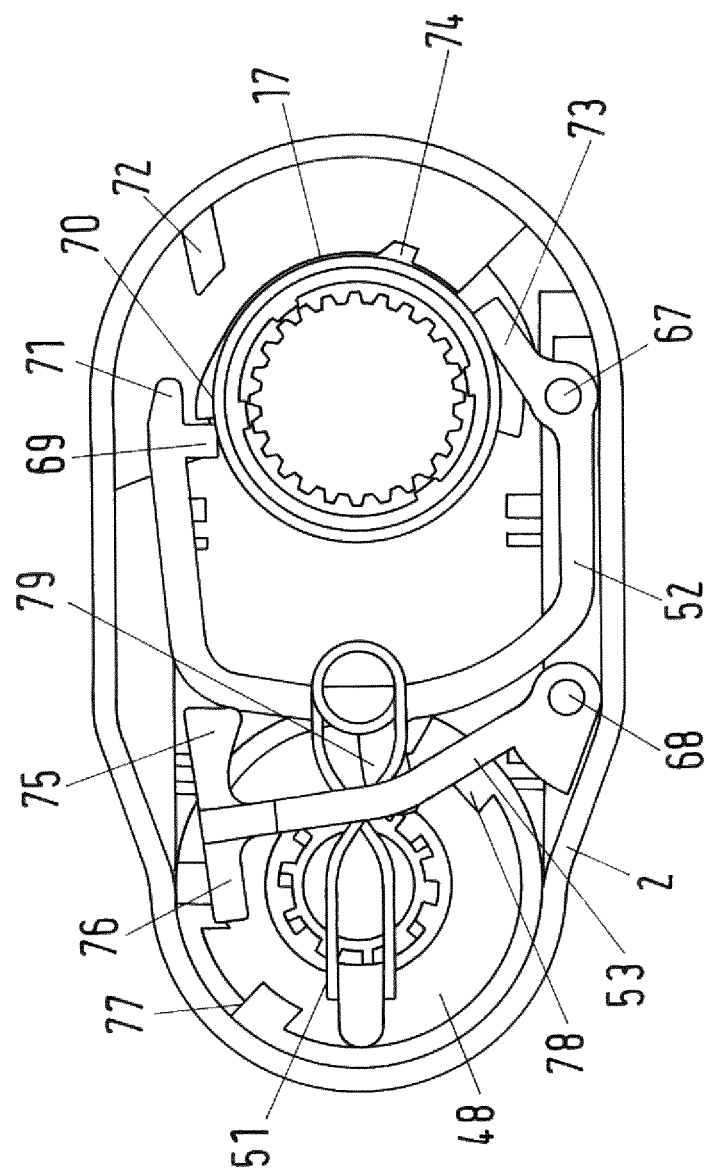
Figure 11A:
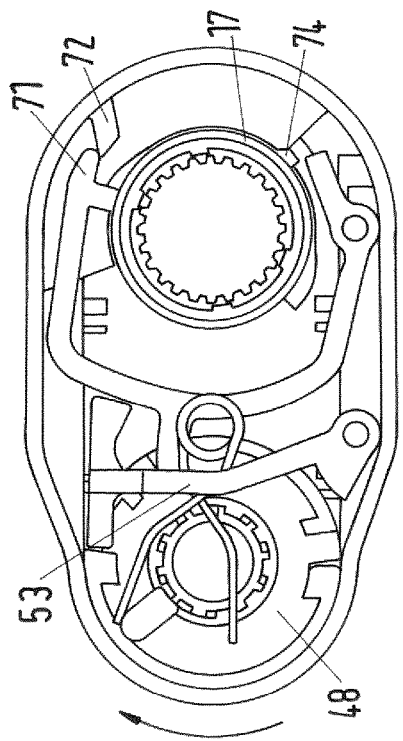
Figure 11B:
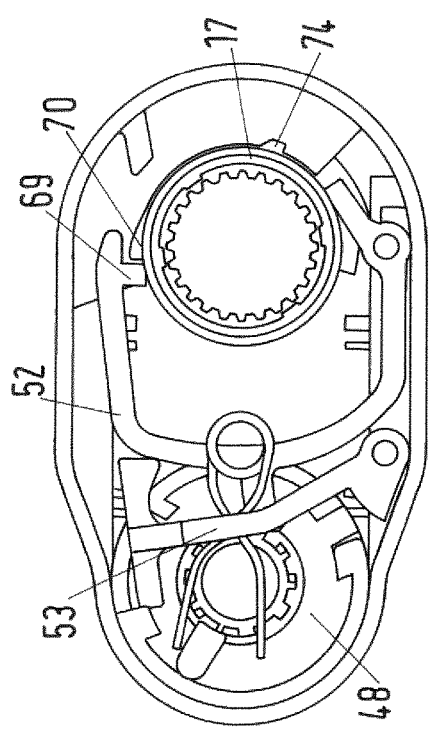
Figure 11C:
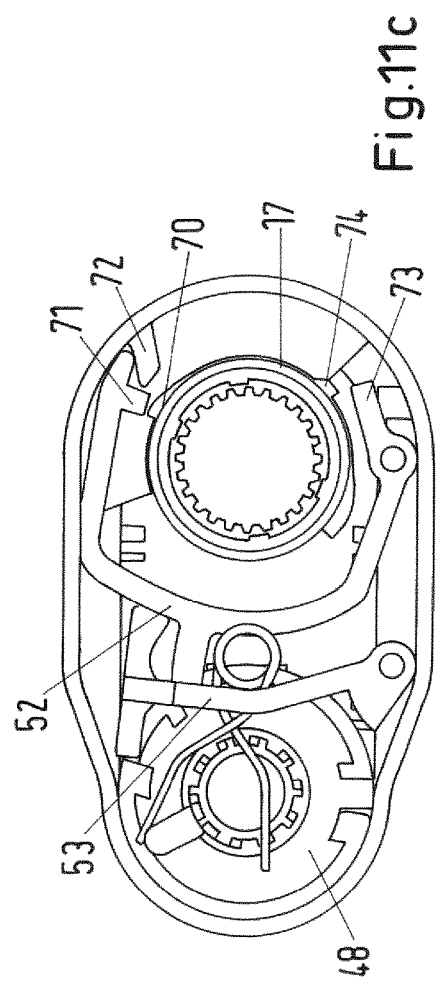
Figure 12:
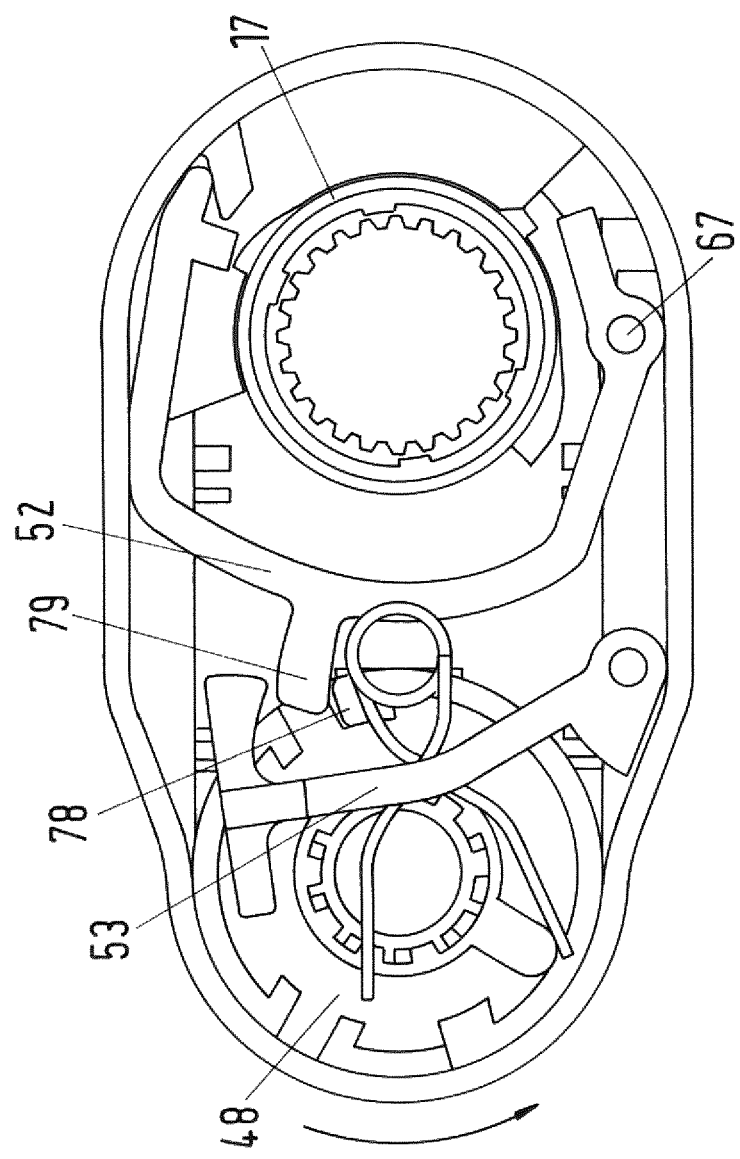
Figure 13:
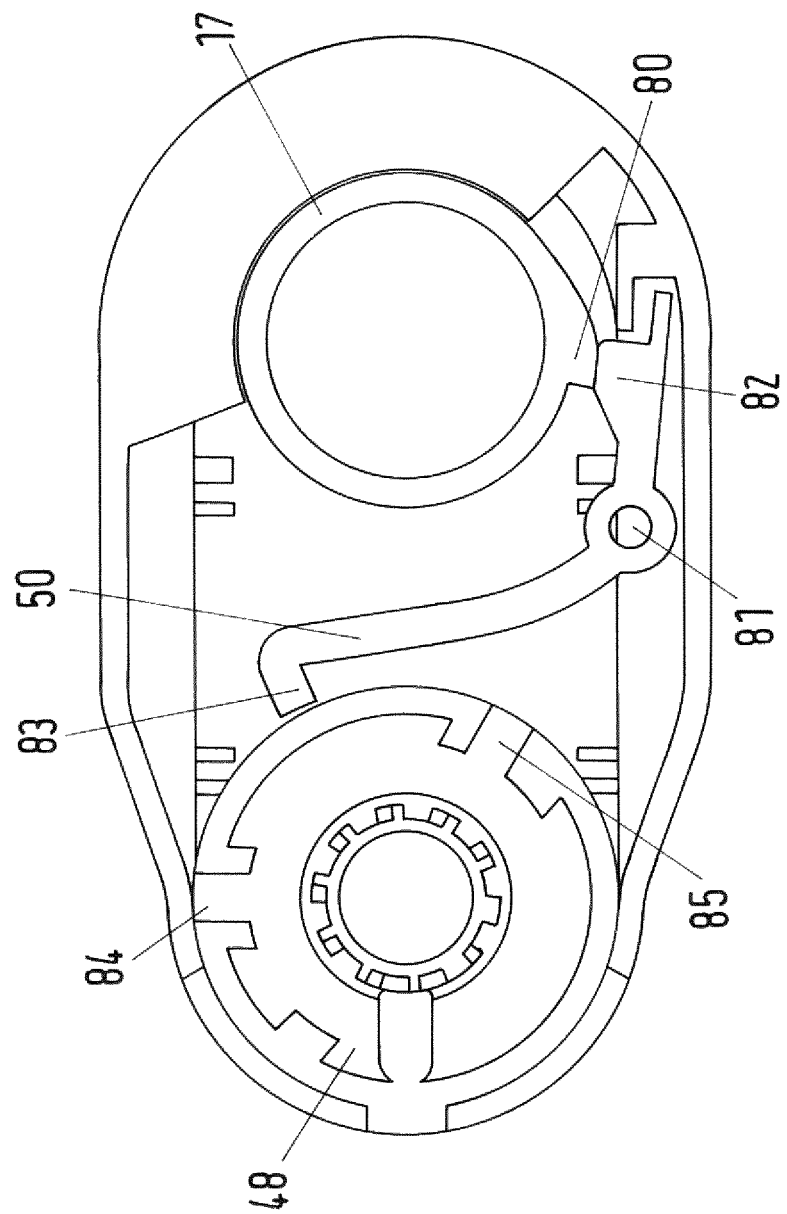
Figure 14:
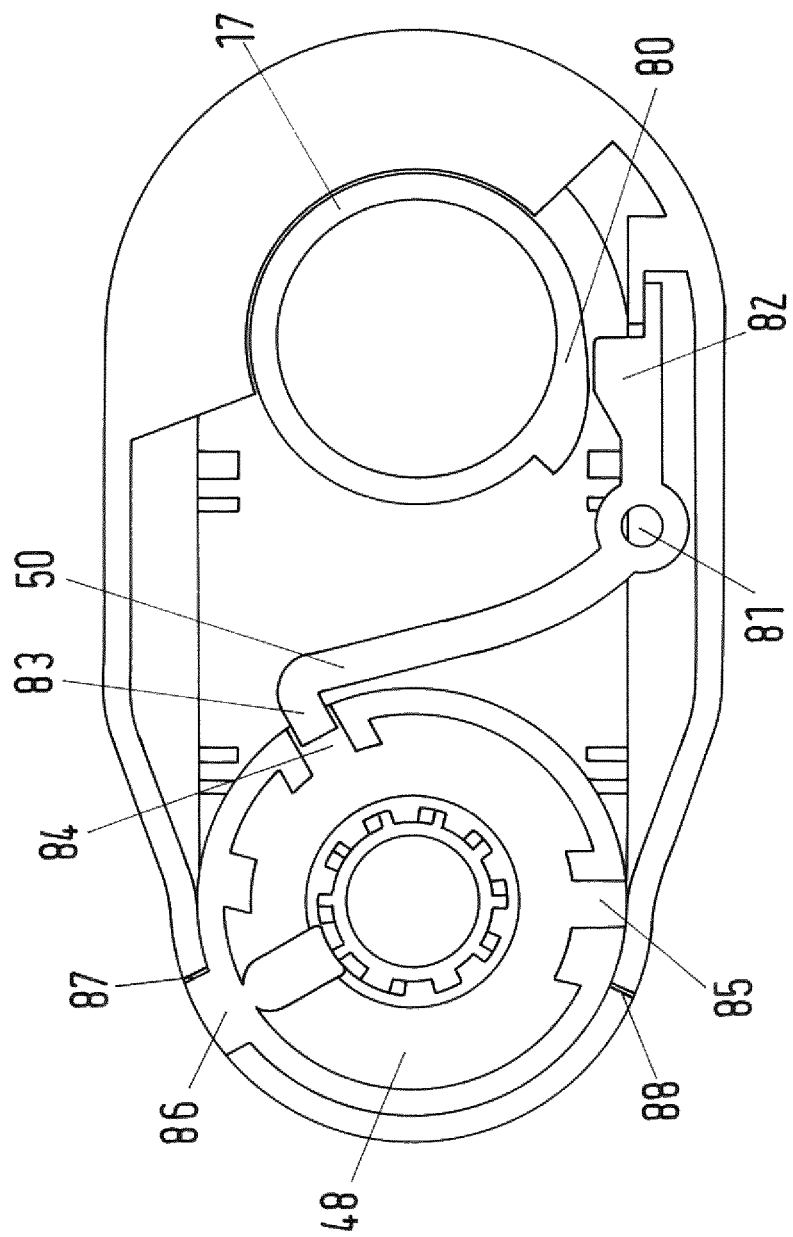
Figure 15:
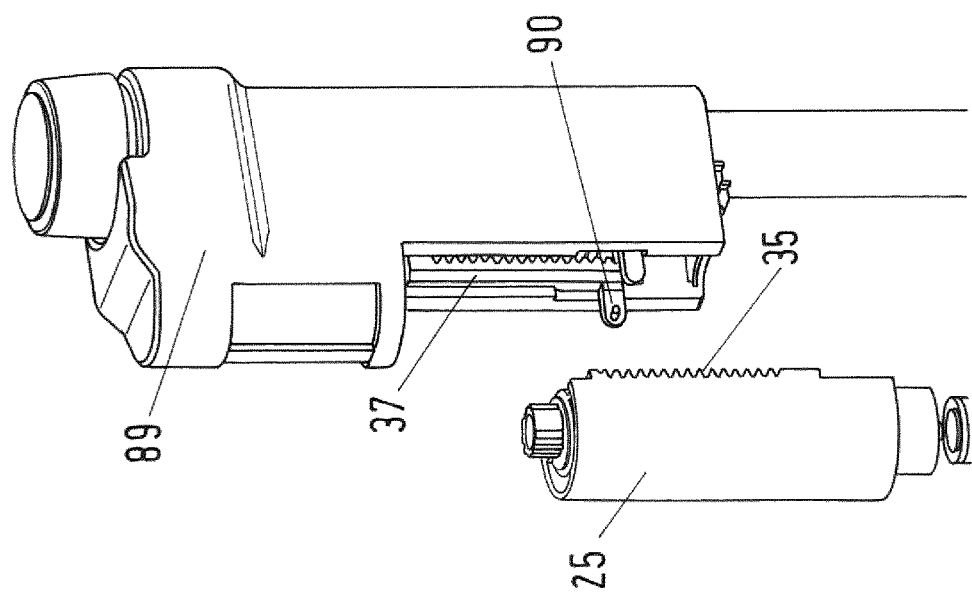

FIG. 8: shows a perspective view part of the secondary drug delivery assembly;

FIG. 9: shows a sectional view another part of the drug delivery device;

FIG. 10: shows a sectional view a further part of the drug delivery device;

FIG. 11a-c: show the elements of FIG. 10 in different conditions;

FIG. 12: shows the element of FIG. 10 in a further condition;

FIG. 13: shows in a sectional view a further part of the drug delivery device in accordance with a further embodiment of the invention;

FIG. 14: shows the elements of FIG. 13 in a further condition;

FIG. 15: shows a drug delivery device in accordance with a further embodiment of the invention;

FIG. 16a, b: show different housing parts of the drug delivery device of FIG. 15.

The drug delivery device 1 comprises a housing 2 in which a primary drug delivery assembly 3 and a secondary drug delivery assembly 4 are retained. The housing 2 extends along a longitudinal axis 5 from a proximal end 6 to a distal end 7 of the drug delivery device 1. A primary reservoir 8 (medicament cartridge) is arranged in the primary drug delivery assembly 3 at its distal end. A secondary reservoir 9 (medicament cartridge) is arranged in the secondary drug delivery assembly 4 at its distal end. Each of the cartridges 8 and 9 is sealed at its distal end by a septum 10. A single dispense interface (not shown) with a single injection needle can be attached to the distal end 7 of the drug delivery device housing 2, the single dispense interface having two proximal needles, each of the needles piercing through one of the septa 10 so that a primary medicament 11 in the primary reservoir 8 and a secondary medicament 12 in the secondary reservoir 9 can be dispensed through the single dispense interface through the injection needle.

At the proximal end of the primary cartridge 8, a bung 13 is provided and at the proximal end of the secondary cartridge 9, a bung 14 is provided. When the single dispense interface is properly attached to the drug delivery device 1 and the bungs 13 and 14 are moved in distal direction, the medicaments 11 and 12 are forced out of the respective reservoir 8, 9 through the single dispense interface.

The primary drug delivery assembly 3 comprises a variable dose setting and dose dispensing mechanism 15 and the secondary drug delivery assembly 4 comprises a fixed dose setting and dispense mechanism 16.

The variable dose setting and dispense mechanism 15 includes a number sleeve (dosing sleeve) 17, a primary drive sleeve 18, a lead screw 19, an inner body 20, a last dose nut 21 and a dial grip 22 (actuation element). The inner body 20 is fixed relative to the housing 2.

The fixed dose mechanism 16 includes a secondary lead screw 23, a secondary drive sleeve 24 and a fixed dose mechanism housing 25. A differential gear mechanism 26 connects the variable dose setting and dispense mechanism 15 and the fixed dose setting and dispense mechanism 16.

When the dose dial grip 22 is rotated about an axis extending from the proximal end to the distal end of the primary drug delivery assembly 3 to set or dial a dose, the dose dial grip 22 is rotationally fixed to the primary number sleeve 17 by means of a clutch (not shown). The number sleeve 17 is in threaded engagement with the inner body 20 via a helical thread such that upon rotation of the dose dial grip 22, the number sleeve 17 is constrained to move relative to the inner body 20 along a helical path. During dose setting, resp. dose dialing, the number sleeve 17 winds out of the inner body 20 in proximal direction.

The primary drive sleeve 18 is a tubular element having different diameter regions and is rotationally locked to the dial grip 22. The primary lead screw 19 is an elongated element with an outer surface 27 having two external threads 28, 29 with opposite hands which overlap each other. The distal region of the primary drive sleeve 18 has an inner thread or projection 32 that engages one of the external threads 28, 29 of the lead screw 19. One of the threads 28, 29 engages an inner thread resp. projection 30 of the inner body 20. A disc-like bearing 31 is provided at the distal end of the lead screw 19. A moveable button 33 is provided at the proximal end of the housing 2.

During dose setting, the dial grip 22, the number sleeve 17 and the primary drive sleeve 18 are rotationally and axially locked by a clutch mechanism (not shown). Clockwise rotation of the dial grip 22 causes the primary drive sleeve 18 to rotate and in doing so, it advances along the lead screw 19 which remains fixed throughout dialing.

When the desired dose is dialed, the dial grip 22 can be depressed in distal direction. Dial grip 22, primary drive sleeve 18 and inner body 20 are rotationally locked, while dial grip 22, primary drive sleeve 18 and number sleeve 17 are axially coupled. The rotational constraint between the dial grip 22 and number sleeve 17 is removed as a result of a small relative axial displacement between them. The dial grip 22, the inner body 20 and primary drive sleeve 18 are rotationally locked. As the dial grip 22 is depressed via the button 33, the primary number sleeve 17 moves along its helical path relative to the inner body 20 in distal direction and the dial grip 22 moves axially with the number sleeve 17 but does not rotate due to its rotational constrain to the inner body 20. Axial movement of the drive sleeve 18 results in the primary lead screw 19 to be driven forward to the dispense drug from the cartridge 8.

In the fixed dose mechanism 16, the secondary drive sleeve 24 is constrained to move relative to the housing 25 along a pre-defined path. The secondary drive sleeve 24 consists of helical segments, alternating with pure axial segments to return the secondary drive sleeve 24 and the fixed dose mechanism housing 25 to the same relative axial position.

During setting of the fixed dose, the secondary drive sleeve 24 moves relative to the housing 25 along a helical path in proximal direction. Once the secondary drive sleeve 24 has reached the end of the helical segment, a fixed dose is set. For dispense, the drive sleeve 24 is moved forward in a pure axial motion in distal direction to deliver the fixed dose. Inner helical segments on the secondary drive sleeve 24 are matched to an outer helical track 34 on the secondary lead screw 23. The secondary lead screw 23 remains stationary during helical motion of the drive sleeve 24 in proximal direction. Axial motion of the secondary drive sleeve 24 causes the secondary lead screw 23 to advance towards the distal end. The bung 14 in the secondary cartridge is moved in distal direction so that the secondary medicament is dispensed.

The dose setting and dose dispense elements of the primary drug delivery assembly 3 and the secondary drug delivery assembly 4 are linked by the differential gear mechanism 26, its components being displayed in FIG. 2 in an explosive view. The differential gear mechanism comprises a first toothing (first gear rack) 35 provided on the fixed dose mechanism housing 25, a second toothing (second gear rack) 36, a third toothing (third gear rack) 37 and a firth toothing (fourth gear rack) 38. Further, a transmission element 39 comprising a first gear wheel 40 and two second gear wheels 41 that are concentrically arranged such that a first gear wheel 40 and the second gear wheels 41 rotate along a common axis of rotation.

The first gear rack 35 is formed on the outside of the fixed dose mechanism housing 25 and also has a gear rack extending in axial direction of the drug delivery device.

The second gear rack 36 is an elongated element having a gear rack at its distal (here left side) end, the gear rack consisting of two sets of toothings respectively arranged side by side in a direction from the distal end of the housing towards the proximal end of the housing. The proximal end of the second gear rack 36 is configured to be axially constrained with respect to the primary number sleeve and has a sleeve-like proximal end section 42. The housing 2 is formed such that the second gear 36 rack is axially guided and is prevented from rotating. The second gear rack may be referred to as the "variable dose rack".

The third gear rack 37 is axially constrained to the secondary drive sleeve 24. It is further accommodated in the housing 2 such that relative rotation with respect to the housing 2 is prevented. The third gear rack 37 may only slide in axial direction of the housing 2. The housing 2 is formed such that the third gear rack 37 is axially guided and is prevented from rotating.

The fourth gear rack 38 is constrained to slide axially relative to the second gear rack 36. The fourth gear rack 38 is formed as part of a sleeve arranged radially inwardly with respect to the second gear rack 36, which is also formed as part of a sleeve. The fourth gear rack 38 is axially guided by the second gear rack 36 such that relative rotation is prevented but relative axial movement is possible. Motion of the fourth gear rack 38 relative to the second gear rack 36 in distal direction is limited by an abutment on the inner surface of the sleeve section of the second gear rack 36.

The transmission element 39 comprises a shaft on which the first gear wheel 40 is formed. The second gear wheels 41 are rotationally supported by the shaft and concentrically arranged with respect to the first gear wheel 40 such that the first gear wheel 40 and the second gear wheels 41 share a common rotational axis. The first gear wheel 40 meshes with both the fourth gear rack 38 and the first gear rack 35. The second gear wheels 41 mesh with both the second gear rack 36 and the third gear rack 37.

The first gear rack 35 may be referred to as the "housing gear rack".

The second gear rack 36 may be referred to as the "variable dose rack".

The third gear rack 37 may be referred to as the "fixed dose rack"

The fourth gear rack 38 may be referred to as the "dosing rack".

The first wheel 40 may be referred to as the "dosing gear".

The second wheels 41 may be referred to as the "variable dose/fixed dose gear".

The interaction of the linear differential gear mechanism components are now described with respect to FIG. 3. The secondary drive sleeve 24 is connected to the third gear rack 37 via an engagement section 43 where a projection of the third gear rack 37 engages a recess in the secondary drive sleeve 24 such that the third gear rack 37 and the secondary drive sleeve 24 are axially constrained. The primary number sleeve 17 has a proximal flange-like engagement section 44, which urges the sleeve section 42 of the second gear rack 36 in proximal direction during dose setting.

When a fixed dose is not set be the delivered, the secondary drive sleeve 24 is not actuated and does not displace in proximal direction. The third gear rack 37 remains stationary. Setting a dose of the primary medicament by operating the dose dial grip 22 results in displacement of the number sleeve 17 and in displacement of the second gear rack 36 in proximal direction. As the second gear rack 36 moves in proximal direction 6, the first gear wheel 40 and the second gear wheel 41 mesh with the associated gear rack. The axial motion of the fourth gear rack 38 is the same axial displacement of the second gear rack 36 so that the fourth gear rack 38 and the second gear rack 36 move together in proximal direction. When a set dose of the primary medicament is injected, the primary number sleeve 17 moves back in distal direction 7 thereby moving the fourth gear rack 38 and the second gear rack 36 back to their initial, so called "at rest" position.

If a fixed dose is set to be delivered, the secondary drive sleeve 24 and the third gear rack 37 are moved in proximal direction relative to the first gear rack 35 and the primary number sleeve 17. Axial motion of the third gear rack 37 causes rotation of the gear wheel 41 and axial movement of the transmission element 39. As a result there is relative axial motion between the second gear rack 36 and the fourth gear rack 38, which is equal to the axial motion of the secondary sleeve 24.

FIG. 4 shows a detailed view of the proximal end of the drug delivery device after a dose in the secondary drug delivery assembly has been set. The button 33 is arranged movable with respect to the dial grip 22 and can move relative to the dial grip 22 between the proximal position as shown in FIG. 4 and a distal position, in which a distal surface of the button 33 engages a proximal surface of the dial element 22. During the setting of a fixed dose, the relative axial motion between the fourth gear rack 38 and the second gear 36 rack results in the fourth gear rack 38 abutting the button 33 and displacing the button 33 relative to the dial grip 22 in proximal direction such that the button 33 protrudes proximally from the dial grip 22 as displayed in FIG. 4.

When the button 33 extends above the dial grip 22, it is indicated that a dose in the secondary drug delivery assembly has been set. Setting of a variable dose can continue through rotation of the dial grip 22 along its helical path which causes the dial grip 22 to move in proximal direction. As the primary number sleeve 17 is displaced helically, the second gear rack 36 is moved in proximal direction. The differential gear mechanism transfers the same axial motion to the fourth gear rack 38 such that the second gear rack 36 and the fourth gear rack 38 move axially together. The relative position between the second gear rack 36 and the fourth gear rack 38 remains constant during the setting of the primary dose of medicament. Due to the abutment between the fourth gear rack 36 and the button 33 and the contact between the first gear wheel 40 and the first gear rack 35, the extension of the button 33 relative to the dial grip 22 is maintained as both components move away from the housing.

When the doses of the primary medicament and the secondary medicament are to be dispensed, the user presses against the proximal face of the button 33. As the button 33 is in an engagement with the fourth gear rack 38, this displacement of the button 33 in distal direction forces the fourth gear rack 38 in the same. The axial motion is transferred via the differential gear mechanism to the third gear rack 37. The force applied to the second gear rack 36 is reacted by the number sleeve 17, which resists axial motion due to an interlock clutch (not shown) between the number sleeve 17 and the dial grip 22. The force applied to the third gear rack 37 is transferred to the secondary drive sleeve 24 such that a fixed dose is dispensed. During dispense of the fixed dose, the button 33 enters back into the dial grip 22. When the button 33 is back in its proximal position, the user force is transferred directly to the dial grip 22 so that dispense of the variable dose of the second medicament begins. Thereby, it is ensured that the set fixed dose of medicament is dispensed prior to the dispense of the variable dose.

During dispensing of the fixed dose, the secondary drive sleeve 24 and the third gear rack 37 displace axially to their initial position. As the third gear rack 37 moves axially and the second gear rack 38 remains stationary, the fourth gear rack 38 and the button 33 move relative to the second gear rack 36 and the dial grip 22 until abutment occurs between the button 33 and the dial grip 22. At this point, the fixed dose is fully dispensed and dispensing of the variable dose can continue with the user force being transferred from the button directly to the dial grip 22. During dispense of the variable dose, the number sleeve 17 winds back into the housing 2 in distal direction along its helical path.

When the button 33 is not extended, the user force is transferred directly to the dial grip 22 and the primary drive sleeve 18 so that the primary medicament is dispensed as described above. The dial grip 22 and the button 33 move axially in distal direction and the second gear rack 36 and the fourth gear rack 38 move axially until the dispensing has been completed. The third gear rack 37 remains stationary.

FIG. 5 shows the dose scale on the number sleeve 17 of the primary drug delivery assembly, which is viewable by the user through a window in the housing. When a variable dose of the primary medicament is dialed, the number sleeve 17 moves along a helical path relative to the housing and the dialed dose is displayed through the window. Two separate dose scales 46, 47 are marked helically on the surface of number sleeve 17 in a parallel relationship. The first dose scale 45 represents the set dose if no fixed dose in the secondary drug delivery assembly is set. The second dose scale 46 represents the set dose as a combination of a dialed variable dose and a fixed dose, resp. a combination of a set dose in the primary drug delivery assembly and a set dose in the secondary drug delivery assembly. In this embodiment, the second dose scale 46 represents an additional 5 units of the parallel first dose scale 45, such that for a given number sleeve position the dose marked onto the second dose scale 46 is 5 units greater than that marked onto the first dose scale 45.

An elongated window (not shown) is provided in the drug delivery device housing through which both dose scales 45, 46 are visible. A masking window 47 (FIG. 6) is incorporated into the third gear rack 37, such that one of the dose scales 45, 46 is obscured from view depending on the axial position of the third gear rack 37. During setting of a fixed dose, the third gear rack 37 is moved in proximal direction relative to the number sleeve 17 as explained above. The masking window 47 displaces in proximal direction, thereby hiding the respective dose unit on first dose scale 45 (e.g. 2 units) and giving view to respective combined dose on the second dose scale 46 (e.g. 7 units). In the meantime, the button 33 projects from the dial grip 22 as explained above.

If a fixed dose has been set, the fixed dose will be dispensed prior to the variable when the button 33 is pressed. The third gear rack 37 moves relative to the housing in distal direction, while the number sleeve 17 remains stationary. The marking window 47 moves from the second dose scale 46 to the first dose scale 45 during delivery of the fixed dose. After the fixed dose has been delivered, the first dose scale 45 is visible to the user and as the variable dose is delivered, the displayed dose will reduce due to rotation of the number sleeve 17 along its helical path.

FIG. 7 displays a fixed dose selection mechanism to enable the user to select whether or not the fixed dose medicament (the secondary medicament) will be dispensed along with the variable dose.

The mechanism is configured such that if a user selects to dispense a dose of the secondary medicament, resp. the fixed dose liquid medicament, the secondary dose setting and dose dispensing mechanism is automatically set to deliver the fixed dose medicament and a predetermined number of units of variable dose liquid medicament. In the embodiment explained below, the predetermined number of units is 5 units. The fixed dose selection mechanism includes a selection switch 48, a clutch 49, a latch lever 50, a spring 51, a first advance lever 52 and a second advance lever 53. These elements interact with the primary number sleeve 17, the secondary drive sleeve 24 and the housing 2 as explained in the following.

As shown in FIG. 8, the clutch 49 comprises a sleeve-like main section 54. Reference numerals 6 and 7 are included to indicate proximal and distal direction when the components are assembled in the drug delivery device. The proximal end 6 of the clutch 49 has a smaller outer diameter than the main section 54 and is provided with a splined outer surface 55 with splines extending in axial direction. The distal end 7 of the clutch 49 has engagement arms 56 in a circular formation around a longitudinal axis 57 of the clutch 49 and extending in axial direction towards the secondary drive sleeve 24. The main section 54 is hollow such that the proximal end of the drive sleeve 24 is insertable into the main section 54.

The proximal end section of the secondary drive sleeve 24 is provided with a number of axially extending grooves 58 that are open at the proximal end such that the radially inner surface of the engagement arms 56 may enter the groove. The radially inner surface of the engagement arms 56 and the grooves 58 form a groove/nut or splined connection by which rotational movement may be transferred between the clutch 49 and the secondary drive sleeve 24, while allowing relative axial movement.

On the outer surface of the main section 54, a pin 59 is formed. The pin 59 forms an interface with a groove 60 on the inside of the fixed dose mechanism housing 25 as shown in FIG. 9. The groove 60 has two sections extending in circumferential direction of the fixed dose mechanism housing 25, wherein the first section 61 is separated from a second section 62 by a sloped or inclined transition 63. Towards the proximal end 6, the first section 61 is set back with respect to the second section 62. The pin 59 can run or slide in the groove 60 from the first section 61 into the second section 62 via the transition 63 and back. Travel of the pin 59 between the sections 61 and 62 causes the clutch 49 to move in axial direction. This interface between the clutch 49 and the fixed dose mechanism housing 25 controls the axial position of the clutch 49 when the clutch 49 is rotated about the longitudinal axis 57. As also obvious from FIG. 9, the fixed dose mechanism housing 25 has projections 64 that engage a recess 65 in the housing 2 of the drug delivery device to ensure the fixated position of fixed dose mechanism housing 25.

The sleeve-like selection switch 48 is supported rotatable in the drug delivery housing 2 and may rotate around the longitudinal axis 57. The clutch 49 is rotationally constrained to the rotation of the selection switch 48 via the splined surface 55, which engages a correspondingly formed inner surface of the selection switch 48 in a splined hole to form a splined interface that allows relative axial movement but prevents relative rotational movement between the clutch 49 and the selection switch 48. The selection switch 48 has a lever surface (not shown) that extends in radial direction through an opening (not shown) in the drug delivery housing 2. The opening is formed such that a user can actuate the lever and rotate the selection switch around the longitudinal axis 57.

The selection switch 48 is rotatable between three positions. The first position is an intermediate "at rest" or central position. In this position, the clutch 49 is in a rotational position relative to the pin 59 as shown in FIG. 9. From the "at rest" position, the user rotates the selection switch to set the device to deliver a fixed dose of the secondary medicament in combination with a variable dose of the primary medicament or a variable dose of the primary medicament only.

When the selection switch 48 is rotated from the intermediate "at rest" position in clockwise direction when viewed from the proximal end 6, the rotation is transferred to the clutch 49 and the pin 59 moves towards the right end in the first section 61 into a second position. The clutch 49 maintains its axial position. This actuation corresponds to the situation in which the user selects to set and inject a dose of the secondary medicament. This position of the selection switch 48 may be referred to a "fixed dose on" position. Rotation of the clutch 49 is transferred to the secondary drive sleeve 24 which rises towards the clutch 49 in a helical movement. If the selection switch 48 is rotated back to the central position, the clutch 49 and secondary drive sleeve rotate in the same direction and the secondary drive sleeve 24 returns along its helical path to unset the set dose. The groove 60 also defines a range, in which the selection switch can be rotated. The maximum value of rotational movement of the selection switch 48, the clutch 49 and the drive sleeve is limited.

When the selection switch 48 is rotated from the intermediate "at rest" position in counterclockwise direction when viewed from the proximal end 6, the pin 59 engages the intermediate section 63 and enters the second section 62 and moves toward the left end of the second section 62 into a third position. This actuation corresponds to the situation in which the user selects not to set and inject a dose of the secondary medicament. This position of the selection switch 48 may be referred to a "fixed dose off" position. The clutch 49 moves axially towards the selection switch 48 due to the inclined intermediate surface and away from the drive sleeve 24 such that the arms disengage from the grooves 58 (FIG. 8) and rotation of the clutch 49 is not transferred to the drive sleeve 24.

During dispense of the fixed dose after setting the selection switch 48 in the "fixed dose on" position, axial movement of the third gear rack is transferred to the secondary drive sleeve 24, which moves in distal direction. Due to the splined engagement between the engagement arms 56 of the clutch 49 and the grooves 60 of the secondary drive sleeve 24, the selection switch 48 and the clutch 49 remain stationary in axial direction during dispense of a dose of the secondary medicament.

As shown in FIG. 8, at the proximal end of the grooves 58, a ratchet element 66 is provided, which engages the engagement arms 56 of the clutch and allows relative rotation between the clutch 49 and the secondary drive sleeve 24 in a first direction and prevents relative rotation in the opposite direction. This ratchet interface enables the clutch 49 to rotate back to its central "at rest" position without causing a rotation of the secondary drive sleeve 24. Further, when the selection switch 48 is moved from its "at rest position" into the "fixed dose off" position, rotation of the clutch 49 is not transferred to the secondary drive sleeve, as the engagement arms 56 merely engage the ratchet element 66 and rotation of the clutch 49 cannot be transferred though the ratchet interface.

In FIG. 10, a sectional view of the drug delivery device from the proximal side end in longitudinal direction is presented. The first advance lever 52 is support by a pin 67 formed on the housing 2 so that the first advance lever 52 can pivot or swivel about an axis running though the pin 67 in viewing direction. The second advance lever 53 is support by a pin 68 formed on the housing 2 so that the second advance lever 53 can pivot or swivel about an axis running though the pin 68 in viewing direction.

The first advance lever 52 is a basically u-shaped element with legs connected by an intermediate section. A first leg has is provided with a first engagement section 69 formed as a projection for engagement with a counter projection resp. a first abutment surface 70 formed on the outer surface of the number sleeve 17. The first leg further ends in a second engagement section 71 formed as a projection for engagement with a counter engagement section 72 formed on the inside of the housing 2. The second leg is provided with an opening to receive the pin 67 and ends in third engagement section 73 for engagement with a second abutment surface 74 formed as a raised boss on the outer surface of the number sleeve 17.

The second advance lever 53 is a t-shaped element with a first section that has at its end an opening to receive the pin 68. The first section ends in a second section that runs substantially perpendicular to the first section. A first projection 75 engages the first advance lever 52 such that the first advance lever 52 swivels or articulates around the pin 67 in clockwise direction when the second advance lever 53 rotates or swivels around the pin 68 in clockwise direction.

Opposite the first projection 75 lies a second projection 76 for engagement with a first abutment surface 77 formed on the selection switch 48, which is shown in FIG. 10 in its "at rest" or central rotational position. Rotation of the selection switch 48 in clockwise direction causes the first abutment surface 77 to engage the second projection 76. As a result, the second advance lever 53 articulates about the pin 68 and the first projection 75 on the second advance lever 53 moves the first advance lever 52 around the pin 67 in clockwise direction. A second abutment surface 78 is provided on the selection switch 48 for engagement with a fourth engagement section 79 on the first advance lever 52. Rotation of the selection switch 48 in counter-clockwise direction causes the second abutment surface 77 to engage the fourth engagement section 79. As a result, the first advance lever 52 articulates about the pin 67 in clockwise direction. Irrespective of whether the selection switch 48 is rotated clockwise or counter-clockwise, the first advance lever 52 swings in the clockwise direction. The spring 51 is located on a pivot within the housing, and provides a restoring force to return the selection switch 48 to its centralized 'at rest' position.

As shown in FIG. 10, the selection switch 48 is in its "at rest position". The distance in rotational direction between the raised boss 74 and the third engagement section 73 is such that the number sleeve 17 can be rotated about a predetermined angular range in clockwise direction. In the described embodiment this angular range corresponds to 2 set units of the primary medicament. When the selection switch is at its "at rest" position, the settable dose in the primary drug delivery assembly is limited to 2 units. The dial grip 22 may only be rotated up to 2 units in clockwise direction. When the dial grip is rotated to 2 units, the boss 74 abuts the third engagement section 73 and prevents further rotation of the number sleeve 17 until the first advance lever 52 is displaced through activation of the selection switch 48 such that the third engagement section 73 is moved away from the boss 74. This mechanism limits a settable dose of the primary medicament to 2 units, which then can be dispensed by depressing the button 33. If the user wishes to dispense a larger variable dose they must activate the selection switch 48.

Rotation of the selection switch 48 ("fixed dose on") in clockwise direction causes the levers 52, 53 to articulate. Simultaneously, the clutch 49 and the secondary drive sleeve 24 are operated and a dose of the secondary medicament is set. The second lever 53 causes the first lever 52 to rotate about the pin 67 so that the third engagement section 73 swings away from the number sleeve 17 and the boss 74 so that the lock between the housing and the number sleeve 17 is removed, allowing the user to continue to dial a variable dose beyond the 2 units limit.

The user may choose to activate the selection switch 48 prior to dialing the dose in the primary drug delivery assembly. With regard to FIGS. 11a to 11c, when the selection switch 48 is rotated into its "fixed dose on" state prior to rotation of the dial grip, the first engagement section 69 engages the first abutment surface 70 on number sleeve 17 causing the number sleeve 17 to rotate in correspondence to 2 units (FIGS. 11a and 11b). The first advance lever 52 articulates in clockwise direction until the second engagement section 71 engages the abutment surface 72 on the housing 2 which causes the first engagement section 69 to move away from the number sleeve 17 at the end of the articulation. The dose of primary medicament that is dialed with the number sleeve 17 corresponds to 2 units. This situation is shown in FIG. 11c. Articulation of the first advance lever also moves the third engagement section 73 away from the number sleeve 17 so that the user is free to dial beyond the 2 units limit of the primary medicament by rotating the dose dial grip. Rotation of selection switch 48 into the "fixed dose on" position is transferred to the clutch 49 as described above and is transferred to the secondary drive sleeve 24 to set a dose of the secondary medicament.

FIG. 12 shows the situation, in which the user chooses not to set and inject a dose of the secondary medicament. The selection switch 48 is rotated from its central "at rest position" in counterclockwise direction to its "fixed dose off" state. Rotation of the selection switch in counterclockwise direction causes the clutch 49 to rotate in counterclockwise direction and to move in proximal direction (see FIG. 8). The secondary drive sleeve 24 remains stationary due the ratchet 66 on the drive sleeve 24 and the axial displacement of the clutch 49. A dose of the secondary medicament is not set. During rotation of the selection switch 48 to the left, the first advance lever 52 is pivoted about the pin 67 by engagement of the second abutment surface 78 on selection switch 48 with the fourth engagement section 79 on the first advance lever 52. 2 units of the primary medicament are set and further dialing of the number sleeve 17 is allowed.

The advance levers 52, 53 are held in their articulated position by their abutments with the selection switch 48. In this embodiment the levers 52, 53 act against sprung pivots, such that they return to their 'at rest' position as shown in FIG. 10 when the selection switch 48 returns to its central position. The levers 52, 53 may be accommodated in the housing in a prestressed condition such that the levers 52, 53 tend to return back to their "at rest" state. Alternatively, the levers 52, 53 may be formed elastically and mounted in the drug delivery device in prestressed condition wherein the prestress forces tend to urge the levers 52, 53 into their "at rest" position.

As shown in FIG. 13, the selection switch 48 is held in the "fixed dose on" or fixed dose off" position by the latch lever 50. The latch lever 50 is provided to restrain the selection switch 48 in its set position, until the latch lever 50 is articulated by the number sleeve 17. The number sleeve 17 is provided with a ramp feature 80 on its outer surface, whose outer surface moves away from the axis of rotation of the number sleeve 17 in circumferential direction. The latch lever 50 is pivotably support in the housing 2 and can pivot around a pivot point 81 around an axis running parallel to the rotational axis of the number sleeve 17. The latch lever 50 comprises two legs extending from the pivot point in different directions. A first engagement section 82 is provided for engagement with the ramp 80 and a projection 83 formed as a latch is provided on the other leg for engagement with either a first slot 84 or a second slot 85 each provided on the selection switch 48, depending on the direction the selection switch 48 is rotated from the "at rest" position. When the selection switch 48 is rotated in clockwise direction, the projection 83 engages the first slot 84. When the selection switch 48 is rotated in counterclockwise direction, the projection 83 engages the second slot 85.

When the number sleeve 17 is at a "at rest" position as shown in FIG. 13 and the number sleeve 17 has not been rotated to set a dose, the ramp feature 80 acts on the engagement section 82 and urges the projection 83 away from the selection switch 48. When the number sleeve 17 is rotated in clockwise direction, the abutment between the ramp 80 and the engagement section 82 is removed as shown in FIG. 14. The latch lever 50 rotates about its sprung pivot point 81 in counterclockwise direction. If the selection switch 48 has not been activated by the user, the latch 83 abuts the outer cylindrical surface of the selection switch 48.

When the selection switch 48 is operated, e.g. by moving the selection switch into the "fixed dose on" state as shown in FIG. 14, the latch 83 engages with the first slot 84, which enables the latch lever 50 to fully rotate about its sprung pivot point 81. The engagement between the latch lever 50 and the selection switch 48 restrains the selection switch 48 in its set position. If the selection switch 48 is moved into the "fixed dose off" state, the latch 83 engages with the second slot 85 and the engagement between the latch lever 50 and the selection switch 48 restrains the selection switch 48 in its "fixed dose off" position.

The selection switch 48 remains in its set position until the latch lever 50 is articulated by the abutment with the ramp 80 of the number sleeve 17. During dispense, the number sleeve 17 rotates backward in distal direction and rotates in counterclockwise direction. At the end of the return movement of the number sleeve 17, the ramp 80 engages the engagement section 82 and the removes the engagement between the latch 83 and he selection switch 48. The selection switch 48 returns to its 'at rest' position under the action of the spring 51 (FIG. 12).

The latch lever 50 is preferably accommodated in the housing in a prestressed condition such that the latch lever 50 tends to pivot against the selection switch 48. Alternatively, the latch lever 50 may be formed elastically and mounted in the housing of the drug delivery device in a prestressed condition wherein the prestress force tends to urge the latch lever 50 against the selection switch about the pivot point 81.

The embodiment in FIG. 14 also shows possible constructive measures which enable to define the value of the fixed dose that can be set with the secondary drug delivery assembly. On the outer surface of the selection switch 48, a selection bar 86 is provided. The selection bar 86 is aligned such that it extends in axial direction 57 as also shown in FIG. 9. The maximum value of rotational movement of the selection switch 48 from the "at rest" position in clockwise direction as well as in counterclockwise direction is limited by the selection bar 86 engaging abutment surfaces 87 and 88 on the housing 2.

In FIG. 15, the housing 2 of the drug delivery device 1 is split into two separable components, a main housing 89 and a second housing, which in this case is the fixed dose mechanism housing 25. The main housing 89 contains the variable dose setting and dose dispense mechanism, the selection switch assembly and the differential gear mechanism, except for the first gear rack 35, which is provided on the fixed dose mechanism housing 25. The fixed dose mechanism housing 25 contains the fixed dose setting and dispense mechanism and the clutch only.

As shown in FIGS. 16*a* and 16*b*, a separable interface is provided between the third gear rack and the secondary drive sleeve in the fixed dose mechanism housing 25 for axial fixation. Arms 90 (FIG. 16*b*) extend from the third gear rack. When the fixed dose mechanism housing 25 is attached to the main housing 89, the arms 90 engage through an aperture 91 (FIG. 16*a*) into a circumferential recess 92 or collar on the outer surface of the drive sleeve 24 such that that the secondary drive sleeve 24 is axially constrained to the third gear rack 37. A separable interface is provided between the selection switch 48 and the clutch 49. The splined outer surface 55 of the clutch 49 is insertable into a splined hole 93 of the selection switch 48. This interface provides a rotational constraint between these components, but allows for relative axial movement.

The fixed dose mechanism housing 25 can be attached to the main housing 89 by latching clips or the like. Releasable connections enable the a sub-assembly relating to a single cartridge, to be discarded and replaced when that cartridge is expended.

REFERENCE NUMERALS 1 drug delivery device
2 housing
3 primary drug delivery assembly
4 secondary drug delivery assembly
5 longitudinal axis of housing
6 proximal end
7 distal end
8 primary reservoir (medicament cartridge)
9 secondary reservoir (medicament cartridge)
10 septum
11 primary medicament
12 secondary medicament
13 bung
14 bung
15 variable dose setting and dispense mechanism
16 fixed dose setting and dispense mechanism
17 number sleeve
18 primary drive sleeve
19 primary lead screw
20 inner body
21 primary last dose nut
22 dial grips (actuation element)
23 secondary lead screw
24 secondary drive sleeve
25 fixed dose mechanism housing
26 differential gear mechanism
27 outer surface
28 thread
29 thread
30 inner thread
31 bearing
32 thread
33 button (movable element)
34 thread
35 first toothing (fixed dose mechanism housing rack)
36 second toothing (second gear rack/variable dose rack)
37 third toothing (third gear rack/fixed dose rack)
38 fourth toothing (fourth gear rack/dosing rack)
39 transmission element
40 first gear wheel ("dose gear")
41 second gear wheel ("variable dose/fixed dose gear")
42 sleeve element
43 engagement section
44 flange-like section
45 first dose scale
46 second dose scale
47 masking window
48 selection switch
49 clutch
50 latch lever
51 spring
52 first advance lever
53 second advance lever
54 main section
55 splined surface
56 engagement arms
57 longitudinal axis
58 grooves
59 pin
60 groove
61 first section
62 second section
63 transition
64 projection
65 recess
66 ratchet
67 pin
68 pin
69 first engagement section
70 first abutment surface on number sleeve
71 second engagement section
72 abutment surface of housing
73 third engagement section
74 second abutment surface on number sleeve (raised boss)
75 first projection
76 second projection
77 first abutment surface on selection switch
78 second abutment surface on selection switch
79 fourth engagement section
80 ramp feature on number sleeve
81 pivot point
82 engagement section on latch lever
83 projection on latch lever (latch)
84 first slot
85 second slot
86 selection bar
87 abutment surface
88 abutment surface
89 main housing
90 arms
91 aperture 92 circumferential recess (collar)
93 splined hole

The invention claimed is:

1. A drug delivery device comprising:
- a primary drug delivery assembly with a primary dose dial sleeve configured to move proximally in a helical movement during setting of a dose of a primary medicament contained in a primary reservoir of the primary drug delivery assembly and a secondary drug delivery assembly with a secondary drive sleeve configured to move in a proximal direction in a helical movement during setting of a dose of a secondary medicament contained in a secondary reservoir of the secondary drug delivery assembly
- a selection switch movable between a first position, a second position, and a third position, wherein the first position is an intermediate position between the second position and the third position; and
- a clutch connected to the selection switch such that movement of the selection switch causes rotation of the clutch,
- wherein the clutch is configured to engage with and to transfer rotation to the secondary drive sleeve when the selection switch is moved from the first position into the second position such that the dose of the secondary medicament is set and to disengage from the secondary drive sleeve when the selection switch is moved from the first position into the third position such that the dose of the secondary medicament is not set, and
- wherein a first engagement element is configured to rotate the primary dose dial sleeve in one direction to set the dose of the primary medicament, wherein the first engagement element is adapted to be engaged by the selection switch such that movement of the selection switch from the first position into the second position and from the first position into the third position causes the first engagement element to rotate the primary dose dial sleeve in the one direction such that a predetermined dose of the primary medicament is set.

2. The drug delivery device according to claim 1, wherein the clutch is movable between a distal position and proximal axial position, wherein the clutch is rotationally constrained to the secondary drive sleeve in the distal position and wherein the clutch is free to rotate relative to the secondary drive sleeve in the proximal position.

3. The drug delivery device according to claim 1 or 2, wherein the clutch is rotationally and axially guided by engagement with a stationary guidance.

4. The drug delivery device according to any of the previous claims, wherein the selection switch is configured to transfer movement to the primary dose dial sleeve such that actuation of the selection switch causes the primary dose dial sleeve to rotate.

5. The drug delivery device according to claim 4, wherein the first engagement element comprises a first engagement section configured to engage a first counter engagement surface on the primary dose dial sleeve.

6. The drug delivery device according to claim 5, wherein the first engagement element comprises a second engagement section that engages a stationary counter engagement section in the second position and/or the third position of the selection switch such that the first engagement section disengages from the primary dose dial sleeve.

7. The drug delivery device according to claim 5 or 6, wherein a second engagement element is arranged between the selection switch and the first engagement element and is configured to transfer movement of the selection switch from the first position into the second position to the first engagement element such that the primary dose dial sleeve is rotated in the one direction.

8. The drug delivery device according to any of claims 5-7, wherein the selection switch engages the first engagement element when the selection switch moves from the first into the third position such that the primary dose dial sleeve is rotated in the one direction.

9. The drug delivery device according to any of claims 5-8, wherein the first engagement element comprises a third engagement section for engagement with a boss on the primary dose dial sleeve when the selection switch is in the first position such that rotation of the primary dose dial sleeve in the one direction is limited.

10. The drug delivery device according to any of the previous claims comprising a biasing member that is configured to bias the selection switch into the first position.

11. The drug delivery device according to any of the previous claims, comprising a latching element that is configured to lock the selection switch in the second position and/or the third position.

12. The drug delivery device according to claim 11, wherein the primary dose dial sleeve is provided with means configured to disengage the latching element from the selection switch when the primary dose dial sleeve rotates in a direction opposite the one direction.

* * * * *